United States Patent
Pastre et al.

(10) Patent No.: US 11,384,351 B2
(45) Date of Patent: Jul. 12, 2022

(54) METHODS AND TOOLS FOR PURIFYING NUCLEIC ACIDS AND USING POLYMERIZED TUBULIN

(71) Applicants: INSERM (INSTITUT NATIONAL DE LA SANTE ET DE LA RECHERCHE MEDICALE), Paris (FR); UNIVERSITE D'EVRY—VAL D'ESSONNE, Evry (FR)

(72) Inventors: David Pastre, Evry (FR); Bénédicte Desforges, Evry (FR); Alexandre Maucuer, Evry (FR)

(73) Assignees: INSERM (INSTITUT NATIONAL DE LA SANTE ET DE LA RECHERCHE MEDICALE), Paris (FR); UNIVERSITE D'EVRY—VAL D'ESSONE, Evry (FR)

( * ) Notice: Subject to any disclaimer, the term of this patent is extended or adjusted under 35 U.S.C. 154(b) by 123 days.

(21) Appl. No.: 16/633,768

(22) PCT Filed: Jul. 27, 2018

(86) PCT No.: PCT/EP2018/070433
§ 371 (c)(1),
(2) Date: Jan. 24, 2020

(87) PCT Pub. No.: WO2019/020798
PCT Pub. Date: Jan. 31, 2019

(65) Prior Publication Data
US 2020/0239870 A1 Jul. 30, 2020

(30) Foreign Application Priority Data

Jul. 27, 2017 (EP) .................... 17306008

(51) Int. Cl.
C12Q 1/68 (2018.01)
C12N 15/10 (2006.01)
C12Q 1/6806 (2018.01)

(52) U.S. Cl.
CPC ....... *C12N 15/1003* (2013.01); *C12Q 1/6806* (2013.01)

(58) Field of Classification Search
None
See application file for complete search history.

(56) References Cited

FOREIGN PATENT DOCUMENTS

WO 2014/072349 A1 5/2014

OTHER PUBLICATIONS

Chuong et al: "Identification of Rice RNA- and Microtubule-binding Protein as the Multifunctional Protein, a Peroxisomal Enzyme Involved in the [beta]-Oxidation of Fatty Acids", Journal of Biological Chemistry, vol. 277, No. 4, pp. 2419-2429, Nov. 12, 2001.*

(Continued)

*Primary Examiner* — Jehanne S Sitton
(74) *Attorney, Agent, or Firm* — WCF IP

(57) ABSTRACT

The present invention relates to the field of nucleic acid purification. In particular, it relates to methods and tools for purifying nucleic acids in a sample; which are compatible with high-throughput sequencing and diagnosis. The inventors have shown that nucleic acid binding proteins recruited to polymerized tubulin (i.e. microtubules) could, subsequently, be isolated from cell lysates. Surprisingly, it has now been found that the amount of recovered nucleic acid found in these microtubule pellets increases dramatically in the presence of nucleic acid-trapping proteins comprising a nucleic acid-binding moiety and a polymerized tubulin-binding moiety, by comparison to proteins devoid of the nucleic acid-binding moiety; and that the recovery of the (Continued)

purified nucleic acids was itself particularly efficient. This purification method is particularly amenable to high-throughput sequencing and/or in the context of a diagnosis method for identifying or comparing the amount of nucleic acids in a set of samples.

12 Claims, 7 Drawing Sheets

Specification includes a Sequence Listing.

(56) References Cited

OTHER PUBLICATIONS

Chuong et al: "The peroxisomal multifunctional protein interacts with cortical microtubules in plant cells", BMC Cell Biology, Biomed Central, vol. 6, No. 1, p. 40, Nov. 28, 2005.

* cited by examiner

METHODS AND TOOLS FOR PURIFYING NUCLEIC ACIDS AND USING POLYMERIZED TUBULIN

FIELD OF THE INVENTION

The invention relates to methods and tools for purifying nucleic acids; and more specifically to purification methods which are amenable to high-throughput sequencing and diagnosis.

BACKGROUND OF THE INVENTION

Molecular diagnostics has become increasingly important. It has found a way into the clinical diagnosis of diseases (inter alia, detection of infectious agents, detection of mutations of the genome, discovery of circulating tumor cells, and identification of risk factors for the predisposition to a disease), but also in veterinary medicine, environmental analysis, and food testing, use is meanwhile being made of molecular diagnostics methods. Tests at pathology/cytology institutes or in the context of forensic problems represent a further area of application. In the context of healthcare (e.g., tests on blood supplies for absence of infectious agents), use is meanwhile being made of gene diagnostics, and lawmakers are planning to regulate such tests by law in the future. Methods which are used in clinical molecular diagnostics (such as, for example, hybridization or amplification techniques, such as the polymerase chain reaction (PCR), transcription-mediated amplification (TMA), ligase chain reaction (LCR), branched DNA (bDNA) or nucleic acid sequence-based amplification (NASBA) technologies) are also part of the routine procedures in basic scientific research.

In particular, nucleic acid analysis opens promising new possibilities in the research and diagnosis of cancers, by determining gene expression in tissues. Thus, for example, microarray systems have opened the possibility of determining the expression of hundreds or even thousands of genes in a single reaction.

For example, and starting from a sample material, purified nucleic acids (i.e. RNA or cDNA) are applied to a chip which comprises corresponding capture oligonucleotides, and so the nucleic acids in the sample can be detected by hybridization. In addition, other methods for detecting nucleic acids in a sample, for example amplification methods such as the polymerase chain reaction (PCR), are also widespread.

A fundamental problem in nucleic acid analysis is sample preparation. The sample to be investigated usually comprises cells or tissue with interfering, partially insoluble constituents (known as debris) which can interfere with the subsequent isolation and analysis of the nucleic acids of interest. Such insoluble constituents occur particularly in the case of nucleic acid isolation from stool/feces, blood, warts, calcified structures (bones), or else heavily necrotic tissue samples. Debris, in the broadest sense, may also include additional soluble components, which should be removed during the isolation of the nucleic acids.

Methods for purifying nucleic acids, especially prior to sequencing, have already been reported in the Art.

For instance, magnetic solid phase supports, such as functionalized beads or particles, have been used for years in methods for reversibly binding nucleic acids (see for reference U.S. Pat. No. 5,705,628 A), for the specific purpose of purifying said nucleic acids.

In addition, magnetic solid phase supports, such as functionalized beads or particles, have been used to remove ribosomal RNA from total RNA samples, prior to sequencing messenger RNA and other non-coding RNA that are present in lower amount than ribosomal RNA.

Also, the RNA immunoprecipitation Sequencing (RIP-Seq) approach consists in mapping sites where proteins are bound to RNA within RNA-protein complexes. In this method, RNA-protein complexes are immunoprecipitated with antibodies targeted to the protein of interest. RNA molecules recovered by immunoprecipitation are then extracted, reverse-transcribed to cDNA, identified and quantified. Alternatively, after partial RNAse digestion, RNA sequences protected though their binding to the protein can then be mapped back to the genome and deep sequencing of cDNA may further provide single-base resolution of bound RNA (see for reference US2002/0004211 A1, which relates to methods for partitioning endogenous cellular mRNA-protein (mRNP) complexes).

Still, there remains a need for efficient methods and tools for purifying nucleic acids, especially from a biological sample, which remain affordable, reproducible, and compatible with high-throughput sequencing and diagnosis.

SUMMARY OF THE INVENTION

According to a first object, the invention relates to a method for purifying nucleic acid molecules in a sample, comprising at least the steps of:

a) contacting said sample with at least one tubulin and one or more nucleic acid-trapping proteins comprising a nucleic acid-binding moiety and a polymerized tubulin-binding moiety, in efficient conditions for forming polymerized tubulin in complex with the said nucleic acid-trapping proteins bound to the said nucleic acids to be purified; and b) recovering the nucleic acid-trapping protein(s) which is/are bound to the nucleic acid molecules, thereby purifying said nucleic acid molecules.

According to another object, the invention relates to a method for characterizing, preferably sequencing, nucleic acid molecules in a sample, comprising at least the steps of:

a) contacting said sample with at least one tubulin and one or more nucleic acid-trapping proteins comprising a nucleic acid-binding moiety and a polymerized tubulin-binding moiety, in efficient conditions for forming polymerized tubulin in complex with the said nucleic acid-trapping proteins bound to the said nucleic acids to be purified;

b) recovering the nucleic acid-trapping protein(s) which is/are bound to the nucleic acid molecules, thereby purifying said nucleic acid molecules;

c) characterizing, preferably sequencing, the purified nucleic acid molecules.

According to another object, the invention relates to a method for comparing the amounts of target nucleic acid molecules between two samples comprising at least the steps of:

a) performing a method as defined above on a first sample by using a selected nucleic acid-trapping protein, so as to obtain a first collection of purified target nucleic acid molecules, b) performing a method as defined above on a second sample by using the same selected nucleic acid-trapping molecule as that used at step a), so as to obtain a second collection of purified target nucleic acid molecules, and c) determining the amount of target nucleic acid molecules comprised in the first collection of purified target nucleic acid molecules and in the second collection of purified target nucleic acid molecules, respectively.

According to another object, the invention relates to a method for preparing an affinity support for purifying nucleic acid molecules contained in a sample, comprising an in vitro step of immobilizing one or more nucleic acid-trapping proteins on polymerized tubulin; wherein the nucleic acid-trapping protein comprises a nucleic acid-binding moiety and a polymerized tubulin-binding moiety.

According to another object, the invention relates to a kit for purifying nucleic acid molecules and/or for preparing an affinity support for purifying nucleic acid molecules, comprising:

a) at least one nucleic acid-trapping protein, and/or a vector comprising an expression cassette for expressing a nucleic acid-trapping protein, and/or a cell expressing a nucleic acid-trapping protein; and b) lyophilized or purified tubulin;

characterized in that the nucleic acid-trapping protein comprises a nucleic acid-binding moiety and a polymerized tubulin-binding moiety.

According to another object, the invention relates to an affinity support for purifying nucleic acid molecules comprising nucleic acid-trapping proteins immobilized on recombinant or synthetic polymerized tubulin, wherein the nucleic acid-trapping protein comprises a nucleic acid-binding moiety and a polymerized tubulin-binding moiety.

DETAILED DESCRIPTION OF THE INVENTION

Figure 1A:
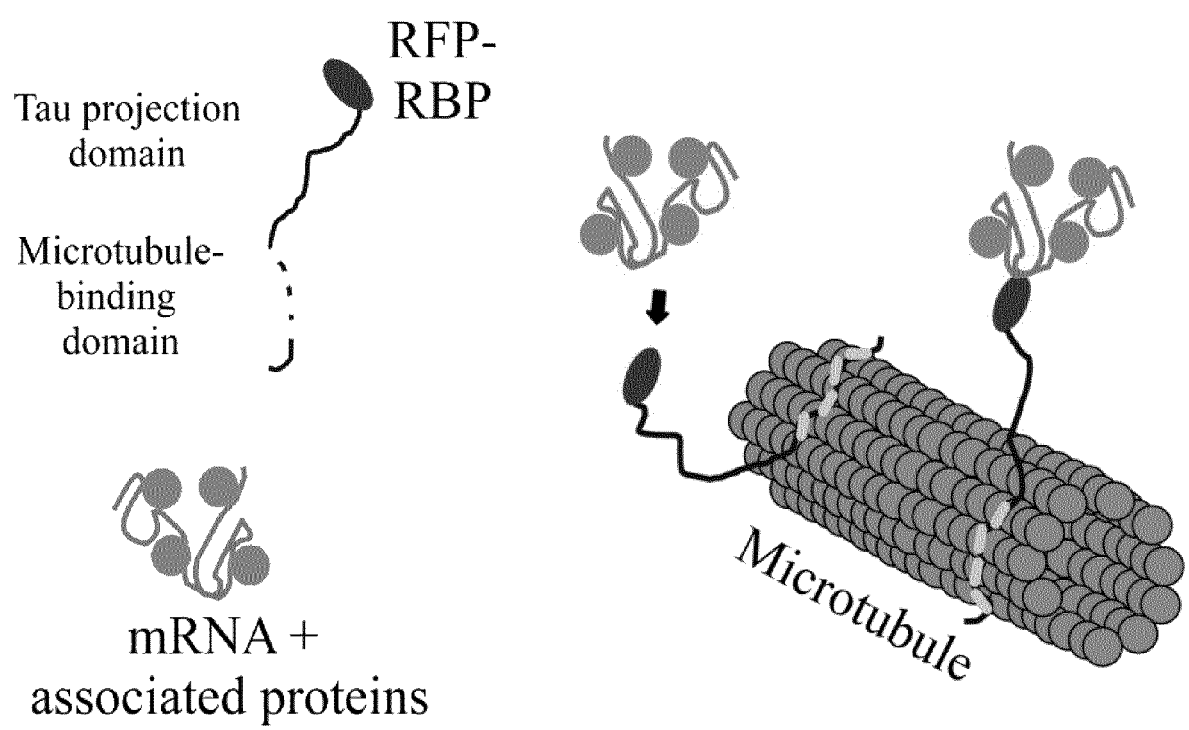
FIG. 1: Microtubule bench and demonstration of RBP functionality. A. Schematic of the method used to bring RBPs on microtubules. B. Schematic of the RT-PCR assays (protocol 1). mRNPs were purified from extracts of Tau-RFP-RBP expressing HEK293T cells by addition of sheep-brain microtubules and centrifugation. C. Schematic of the RT-PCR assays (protocol 2). mRNPs were purified from extracts of Tau-RFP-RBP expressing HEK293T cells by addition of unpolymerized tubulin, in condition suitable for tubulin polymerization, and centrifugation.

The invention has for purpose to meet the above-mentioned needs.

As used herein, the expression "comprising" or "comprises" also includes "consisting" or "consisting of".

As used herein, the expression "at least one" also includes «one», or «more than one», or «a plurality».

As used herein, a "sample" may refer to any sample, especially to any biological sample, susceptible to contain nucleic acids. This may, in particular, encompass any sample comprising or consisting of a cell, a cell lysate, and/or a biological fluid. In a non exclusive manner, a sample may thus consist of a cell or cell lysate, such as a prokaryotic or eukaryotic cell, or lysate thereof. Such samples can thus be, but are not limited to, body fluid (e.g., blood, blood plasma, serum, or urine), organs, tissues, fractions, and cells isolated from mammals including, humans. Biological samples also may include sections of the biological sample including tissues (e.g., sectional portions of an organ or tissue). Biological samples may also include extracts from a biological sample, for example, a biological sample further containing an antigen from a biological fluid (e.g., blood or urine). A biological sample may be of prokaryotic origin or eukaryotic origin (e.g., insects, protozoa, birds, fish, reptiles). In some embodiments, the biological sample is mammalian (e.g., rat, mouse, cow, dog, donkey, guinea pig, or rabbit). In certain embodiments, the biological sample is of primate origin (e.g., example, chimpanzee, or human).

As used herein, the expression "purifying nucleic acids" includes purifying nucleic acid molecules in a free form and/or a bound form (i.e. in complex with nucleic-acid binding molecules).

As used herein, a "nucleic acid-trapping protein" comprises at least one nucleic acid-binding moiety and at least one (preferably more than one) polymerized tubulin-binding moiety.

As used herein, the expression «nucleic acid» or «nucleic acid molecule» may include any form of nucleic acid that is suitable for purification in a sample, which includes, in a non-exclusive manner, DNA and RNA, in particular genomic DNA, plasmid DNA, and also PCR fragments, cDNA, mRNA, miRNA, siRNA, and also oligonucleotides and modified nucleic acids such as, for example, PMA or LMA. It is also possible to purify viral or bacterial RNA and DNA or nucleic acids from human, animal or plant sources, and/or unmodified nucleic acids; but also non-naturally occurring and/or modified nucleic acids, such as nucleic acid molecules including nucleic acid analogues and/or DNA/RNA hybrids. Preferably, the nucleic acids which are considered herein include nucleic acids of the RNA type; which may include modified and unmodified RNA molecules, such as methylated and non-methylated RNA.

Nucleic acids which may be purified by the methods and tools according to the invention may be present in body fluids such as blood, urine, stool, saliva, sputum, or other body fluids, in biological sources such as tissue, cells, in particular animal cells, human cells, plant cells, bacterial cells and the like, organs such as liver, kidneys or lungs, etc. In addition, the nucleic acid may be obtained from support materials such as swabs, pap smears, and stabilizing media such as the methanol-water solution sold under the trademark PRESERVCYT® or the liquid-based Pap test sold under the trademark SUREPATH®, or else from other liquids such as, for example, juices, aqueous samples or food in general. In addition, the nucleic acids may be obtained from plant material, bacterial lysates, paraffin-embedded tissue, aqueous solutions or gels.

As used herein, a "polymerized-tubulin binding moiety" comprises a compound (which is generally a peptide, a protein, or a nucleoprotein) which has the ability to bind specifically to polymerized tubulin. Yet, the said moiety may also bind tubulin in a non-polymerized form. According to one embodiment, the "polymerized-tubulin binding moiety" binds with a higher specificity to tubulin in its polymeric form than to tubulin in its non-polymeric form, which includes its monomeric form and/or its heterodimeric form (which corresponds to the alpha/beta tubulin heterodimer). For instance, a polymerized-tubulin binding moiety may bind mostly or even exclusively to polymerized-tubulin (such as microtubules).

Microtubules are a component of the cytoskeleton, found throughout the cytoplasm. Microtubules are part of a structural network (the "cytoskeleton") within the cell's cytoplasm. The primary role of the microtubule cytoskeleton is mechanical support, although microtubules also take part in many other processes. Thus, microtubules are only part of the so-called "microtubule cytoskeleton", because the latter further includes associated proteins, such as Microtubule-Associated Proteins (MAPs) along with other organizing structures such as the centrosomes.

"Polymerized tubulin" or "Polymerized-tubulin" refers exclusively to the assembly of monomeric tubulin, or alternatively of the assembly of heterodimers of tubulin, in a regular fashion and with a distinct polarity.

Tubular polymers of tubulin can grow as long as 50 micrometres, with an average length of 25 µm, and are highly dynamic. The outer diameter of a microtubule is generally of about 24-25 nm while the inner diameter is of about 12 nm. They are found in eukaryotic cells and are formed by the polymerization of a dimer of two globular proteins, α-tubulin and β-tubulin. Thus, the expression "polymerized tubulin" encompasses microtubules.

Thus, "microtubules" represent a particular rearrangement of "polymerized tubulin", which occurs physiologically in eukaryotic cells, and which forms with additional partners the "microtubule cytoskeleton". The physiological assembly of microtubules is generally described as comprising a first step of regulated assembly of α-tubulin and β-tubulin heterodimers, which together form a polarized protofilament. Then, protofilaments are believed to assemble, as a cylinder, into the so-called microtubule. Thus, microtubules are generally described as polymers of dimers of α- and β-tubulin, which are composed of 13 protofilaments assembled around a hollow core. However, it shall be noted that so-called microtubules with a different number of protofilaments have also been described in the Art, such as microtubules with 14 or 15 protofilaments. However, the physiological meaning of such variations, or "protofilament transitions", remains unclear.

The man skilled in the Art knows that tubulin is one of several members of a small family of globular proteins. The tubulin superfamily includes five distinct families, the alpha-, beta-, gamma-, delta-, and epsilon-tubulins and a sixth family (zeta-tubulin) which is present only in kinetoplastid protozoa. The most common members of the tubulin family are alpha-tubulin (α-tubulin) and beta-tubulin (β-tubulin), the proteins that make up microtubules. The end of the microtubule which corresponds to beta-tubulin is called the plus-end. The end of the microtubule which corresponds to alpha-tubulin is called the minus-end.

Thus, a "polymerized-tubulin binding moiety" of the invention may include an alpha-tubulin and/or a beta-tubulin binding moiety and/or combinations thereof, and binds preferably to tubulin in its polymeric form rather than its monomeric form or its heterodimeric form.

As known in the Art, the "heterodimeric form" of tubulin corresponds to the alpha/beta tubulin heterodimer. Thus, the polymeric form of tubulin also corresponds to a polymer of heterodimers, which also corresponds to more than one heterodimer of alpha/beta tubulin.

For reference, human alpha-tubulin is of sequence: SEQ ID No 7.

For reference, human beta-tubulin is of sequence: SEQ ID No 8.

Unless specified, "tubulin" refers both to polymerized tubulin and non-polymerized tubulin.

As used herein, an «affinity support» or «solid support» refers to a support or matrix in affinity purification, which includes a material to which a specific ligand is covalently or non-covalently bound. Accordingly, the invention also relates to the use of polymerized-tubulin complexed with nucleic acid-trapping protein(s) comprising a nucleic acid-binding moiety and a polymerized tubulin-binding moiety for the preparation of an affinity support.

WO2016/012451 A1 and Boca et al. (Probing protein interactions in living mammalian cells on a microtubule bench. Scientific reports 5, 17304 (2015)) teach methods and tools for detecting interactions in eukaryotic cells using microtubule structures and dynamics. Yet, those documents are totally silent on in vitro purification methods, especially including a step of recovering or collecting purified nucleic acids, even less methods which are amenable to high-throughput sequencing.

The inventors speculated that nucleic acid binding proteins (i.e. RNA-binding proteins or RBPs) recruited in vivo to microtubules could, also, be isolated from cell lysates in vitro. To this end, lysates of tau-RBP expressing cells were incubated with sheep brain microtubules. Nucleoproteins interacting with said microtubules were then pelleted and the nucleic acid content (i.e. the RNA content) analyzed (i.e. by RT-PCR).

Surprisingly, it has now been found that the amount of recovered nucleic acid (i.e. RNA) found in these microtubule pellets increases dramatically in the presence of nucleic acid-trapping proteins comprising a nucleic acid-binding moiety and a polymerized tubulin-binding moiety, by comparison to fusion proteins devoid of the nucleic acid-binding moiety; and that the recovery of the purified nucleic acids was itself particularly efficient.

This purification method is also particularly amenable to high-throughput sequencing and/or in the context of a diagnosis method for identifying or comparing the amount of nucleic acids in a set of samples (i.e. cell lysates).

Without wishing to be bound by the theory, the inventors are of the opinion that polymerized tubulin (i.e. in the form of microtubules) thus provides a number of advantages for nucleic acid purification over known alternative solid supports and methods.

Firstly, polymerized tubulin (i.e. microtubules) offers a large surface for bait proteins in complex with a nucleic acid which is superior to commercially available beads/particles, owing to their dimensions (25 nm in diameter and tenth of micrometers in length). If we consider one hundred 10 µm-long microtubules in typical mammalian cells like HeLa cells, the microtubule surface is larger than 30 µm$^2$ and can even be larger in cells like neurons or muscle cells. Thus, such large surface is available for the binding of an enormous number of baits without saturation (if the bait requires an interacting surface as large as 10 nm$^2$ on microtubules, virtually, more than 3 000 000 bait copies per cell can theoretically be anchored to microtubules). This is significantly higher than the typical number of over-expressed proteins in transfected mammalian cells (about 100 000 copies is already a large over-expression for most proteins.

Secondly, tubulin itself is a well-known protein in the Art which is soluble and which can be produced in a purified or lyophilized form, and which can also be introduced exogenously in a recombinant or in a synthetic manner.

Thirdly, an advantage of using the microtubule surface lies in its dynamic behavior. Microtubules are intrinsically highly dynamics and alternate permanently between shortening and growing phases. This behavior allows to dissociate the bait from microtubules during the depolymerization phase and to bind to another microtubule or after repolymerization of the tubulin. During that interval of time, the bait moves away from microtubules and is then able to capture preys that are located in the medium and not at the vicinity of microtubules. Microtubule-stabilizing drugs such as taxol and Microtubule-disrupting or Microtubule-depolymerizing drugs, such as Nocodazole, Vinblastine, Vincristine, Colchicine, Colcemid, Podophyllotoxin, Rizhoxin or Vinorelbine, can also be used for that purpose.

Fourthly, polymerized tubulin (i.e. microtubules) is a negatively charged structure, a chemical property also shared with nucleic acids (i.e. RNAs). Accordingly, and in the absence of a bait such as a nucleic acid-trapping protein, unspecific binding of said nucleic acids to polymerized tubulin is less favorable, which thus avoids high signal background in contrast to other affinity (solid) supports such as oligo dT beads, and/or those which are generally used for immunoprecipitation.

The method is thus defined by the occurrence of a, preferably reversible, binding between (i) the nucleic acid-binding moiety and the nucleic acid(s) to be purified on one hand; and (ii) the polymerized tubulin-binding moiety and polymerized tubulin on the other hand.

An affinity support comprising, or even consisting of, said polymerized-tubulin complexed with nucleic acid-trapping protein(s) is further detailed hereafter; along with methods of preparation and particular kits and/or nucleic-acid trapping proteins suitable for said methods.

Methods for Purifying and/or Characterizing Nucleic Acid Molecules; and Kits Thereof The invention relates to a method for purifying nucleic acid molecules in a sample, comprising at least the steps of:

a) providing polymerized tubulin in complex with one or more nucleic acid-trapping proteins bound to nucleic acid molecules susceptible to be present in the sample, wherein the nucleic acid-trapping protein(s) comprise(s) a nucleic acid-binding moiety and a polymerized tubulin-binding moiety;

b) recovering the nucleic acid-trapping protein(s) which is/are bound to the nucleic acid molecules, thereby purifying said nucleic acid molecules.

Thus, according to a first object, the invention relates to a method for purifying nucleic acid molecules in a sample, comprising at least the steps of:

a) contacting said sample with at least one tubulin and one or more nucleic acid-trapping proteins comprising a nucleic acid-binding moiety and a polymerized tubulin-binding moiety, in efficient conditions for forming polymerized tubulin in complex with the said nucleic acid-trapping proteins bound to the said nucleic acids to be purified;

b) recovering the nucleic acid-trapping protein(s) which is/are bound to the nucleic acid molecules, thereby purifying said nucleic acid molecules.

Typically, tubulin polymerizes in the form of microtubules, as previously defined. Thus, the invention also relates to the said method for purifying nucleic acid molecules in a sample, comprising at least the steps of:

a) providing microtubules in complex with one or more nucleic acid-trapping proteins bound to nucleic acid molecules susceptible to be present in the sample, wherein the nucleic acid-trapping protein(s) comprise(s) a nucleic acid-binding moiety and a microtubule-binding moiety;

b) recovering the nucleic acid-trapping protein(s) which is/are bound to the nucleic acid molecules, thereby purifying said nucleic acid molecules.

Thus, the invention further relates to a method for purifying nucleic acid molecules in a sample, comprising at least the steps of:

a) contacting said sample with at least one tubulin and one or more nucleic acid-trapping proteins comprising a nucleic acid-binding moiety and a microtubule-binding moiety, in efficient conditions for forming microtubules in complex with the said nucleic acid-trapping proteins bound to the said nucleic acids to be purified;

b) recovering the nucleic acid-trapping protein(s) which is/are bound to the nucleic acid molecules, thereby purifying said nucleic acid molecules.

The nucleic acid molecule to be purified is/are preferably RNA molecule(s) and the nucleic acid-trapping protein(s) is/are RNA-trapping protein(s).

Also, according to one particular embodiment, the nucleic acid-trapping proteins are immobilized on tubulin under conditions suitable for tubulin polymerization.

Indeed, the inventors are of the opinion that the occurrence of a binding of the the polymerized tubulin-binding moiety to tubulin prior to polymerization, or during polymerization, may increase the probability of occurrence of said binding; and hence improve the efficiency of the step of recovery of nucleic acids.

Otherwise said, the polymerized-tubulin binding moiety may bind either to polymerized tubulin (i.e. microtubules) prior to the recovery step, or alternatively to non-polymerized tubulin (i.e. monomeric tubulin) prior to the said recovery step.

In addition, the invention relates to a method as defined above, comprising at least one step of depolymerizing tubulin using a microtubule-depolymerizing drug or cold exposure. Microtubule-disrupting, Microtubule-depolymerizing or Microtubule-disassembling drugs, such as Nocodazole, Vinblastine, Vincristine, Colchicine, Colcemid, Podophyllotoxin, Rizhoxin or Vinorelbine, can also be used for that purpose. Cold exposure is known in the Art and generally relates to a step of depolymeryzing microtubules by exposing them to low temperature. Protocols which relate to cold exposure are known in the Art, and for instance are taught in Ochoa et al. (Cold exposure reveals two populations of microtubules in pulmonary endothelia; Am. J. physiol. Lung Cell. Mol. Physiol.; 300:L132-L138; 2011).

Steps of polymerization and depolymerization as defined above may be advantageously repeated over time, leading to a succession of alternating phases of association and dissociation of the polymerized-tubulin binding moiety over time.

In view of the above, at least four non mutually-exclusive alternative embodiments are envisioned herein, wherein:

a first binding occurs between the nucleic acid-binding moiety and the nucleic acid to be purified, and a second binding occurs between the polymerized tubulin-binding moiety and polymerized tubulin; and/or a first binding occurs between the polymerized tubulin-binding moiety and polymerized tubulin, and a second binding occurs between the nucleic acid-binding moiety and the nucleic acid to be purified; and/or a first binding occurs between the nucleic acid-binding moiety and the nucleic acid to be purified, and a second binding occurs between the polymerized tubulin-binding moiety and tubulin under conditions suitable for tubulin polymerization; and/or a first binding occurs between the polymerized tubulin-binding moiety and tubulin under conditions suitable for tubulin polymerization, and a second binding occurs between the nucleic acid-binding moiety and the nucleic acid to be purified.

The method for purifying nucleic acids which is disclosed herein may also include only in vitro steps, or alternatively both in vivo and in vitro steps.

Thus, according to one preferred embodiment, a method for purifying nucleic acid molecules as disclosed herein includes at least one in vitro step, wherein one or more polymerized tubulin or microtubule binds to the polymerized tubulin-binding or microtubule binding moiety.

Accordingly, the step of bringing into contact the said nucleic acids with the one or more nucleic acid-trapping proteins and tubulin is preferably an in vitro step.

According to one particular embodiment, the invention relates to a method for purifying nucleic acid molecules as defined above, wherein:

the said nucleic acid-trapping proteins are added in vitro to the said sample prior to immobilization on polymerized tubulin; or the sample comprises cells, preferably eukaryotic cells, expressing said nucleic acid-trapping proteins; or a cell lysate thereof.

Thus, according to one embodiment, tubulin (either in polymerized or non-polymerized form) may be present endogenously in the sample from which nucleic acids are to be purified. Alternatively, tubulin may also be exogenously introduced.

According to another non-mutually exclusive embodiment, the polymerized tubulin is exogenously added to the sample susceptible to contain nucleic acids to be purified; or the sample susceptible to contain said nucleic acids comprises cells (preferably eukaryotic cells) expressing said tubulin; or a cell lysate thereof.

According to another non-mutually exclusive embodiment, the sample susceptible to contain said nucleic acids comprises cells (preferably eukaryotic cells), expressing said nucleic-acid trapping proteins; or a cell lysate thereof.

According to another non-mutually exclusive embodiment, the step of providing nucleic acid-trapping proteins consists in expressing the said one or more nucleic acid-trapping proteins in cells, preferably eukaryotic cells.

Thus, according to one embodiment, the method for purifying nucleic acids further comprises at least the steps:

a0) expressing one or more nucleic acid-trapping proteins in eukaryotic cells, a1) preparing a cell lysate from the eukaryotic cells of step a0), a2) bringing into contact the nucleic acid-trapping protein(s) contained in the cell lysate obtained at step a1) with polymerized tubulin and nucleic acid molecules, thereby providing polymerized tubulin in complex with nucleic acid-trapping proteins bound to the nucleic acids to be purified.

Thus, according to said embodiment, the method for purifying nucleic acids comprises at least the steps of:

a0) expressing one or more nucleic acid-trapping proteins in eukaryotic cells, a1) preparing a cell lysate from the eukaryotic cells of step a0), a2) bringing into contact the nucleic acid-trapping protein(s) contained in the cell lysate obtained at step a1) with polymerized tubulin and nucleic acid molecules.

b) recovering the nucleic acid-trapping protein(s) which is/are bound to the nucleic acid molecules; thereby purifying said nucleic acid molecules.

In a non-exclusive manner, the step of recovering the nucleic acid-trapping protein(s) which is/are bound to the nucleic acid molecules is preferably achieved through centrifugation or ultracentifugation. Alternatively, the step of recovering may be achieved through precipitation of the polymerized tubulin; in particular through immunoprecipitation. Such immunoprecipitation may be obtained through a step of binding the polymerized tubulin to a second polymerized-tubulin binding moiety (i.e. an antibody) bound to a solid support (i.e. microbeads).

According to one embodiment, the recovery step consists of at least one (preferably a plurality) of centrifugation and/or precipitation and/or immunoprecipitation steps.

According to one, non-mutually exclusive, embodiment, the method for purifying nucleic acids comprises a further step of collecting the nucleic acid molecules which are complexed with the nucleic acid-trapping protein(s).

Thus, according to one particular embodiment, the invention relates to a method for purifying nucleic acid molecules in a sample, comprising at least the steps of:

a) providing polymerized tubulin in complex with one or more nucleic acid-trapping proteins bound to nucleic acid molecules susceptible to be present in a sample, wherein the nucleic acid-trapping protein(s) comprise(s) a nucleic acid-binding moiety and a polymerized tubulin-binding moiety;

b) recovering the nucleic acid-trapping protein(s) which is/are bound to the nucleic acid molecules;

c) collecting the nucleic acid molecules which are bound to the nucleic acid-trapping protein(s), thereby purifying said nucleic acid molecules.

Thus, according to said particular embodiment, the invention relates to a method for purifying nucleic acid molecules in a sample, comprising at least the steps of:

a) contacting said sample with at least one tubulin and one or more nucleic acid-trapping proteins comprising a nucleic acid-binding moiety and a polymerized tubulin-binding moiety, in efficient conditions for forming polymerized tubulin in complex with the said nucleic acid-trapping proteins bound to the said nucleic acids to be purified;

b) recovering the nucleic acid-trapping protein(s) which is/are bound to the nucleic acid molecules;

c) collecting the nucleic acid molecules which are bound to the nucleic acid-trapping protein(s), thereby purifying said nucleic acid molecules.

According to one, non-mutually exclusive, embodiment, the method for purifying nucleic acids comprises a further step of characterizing, preferably sequencing, the purified nucleic acid molecules.

Thus, the invention as defined above also relates to a method for purifying nucleic acids, for characterizing, preferably sequencing, said nucleic acids.

According to one embodiment, the invention relates to a method for characterizing, preferably sequencing, nucleic acid molecules in a sample, comprising at least the steps of:

a) providing polymerized tubulin in complex with one or more nucleic acid-trapping proteins bound to nucleic acid molecules susceptible to be present in the sample, wherein the nucleic acid-trapping protein(s) comprise(s) a nucleic acid-binding moiety and a polymerized tubulin-binding moiety;

b) recovering the nucleic acid-trapping protein(s) which is/are bound to the nucleic acid molecules, thereby purifying said nucleic acid molecules;

c) characterizing, preferably sequencing, the purified nucleic acid molecules.

Thus, according to said particular embodiment, the invention relates to a method for characterizing, preferably sequencing, nucleic acid molecules in a sample, comprising at least the steps of:

a) contacting said sample with at least one tubulin and one or more nucleic acid-trapping proteins comprising a nucleic acid-binding moiety and a polymerized tubulin-binding moiety, in efficient conditions for forming polymerized tubulin in complex with the said nucleic acid-trapping proteins bound to the said nucleic acids to be purified;

b) recovering the nucleic acid-trapping protein(s) which is/are bound to the nucleic acid molecules, thereby purifying said nucleic acid molecule;

c) characterizing, preferably sequencing, the purified nucleic acid molecules.

According to one, non-mutually exclusive, embodiment, the method for characterizing nucleic acids comprises a further step of collecting the nucleic acid molecules which are complexed with the nucleic acid-trapping protein(s).

Thus, according to one particular embodiment, the invention also relates to a method for characterizing, preferably sequencing, nucleic acid molecules in a sample, comprising at least the steps of:

a) providing polymerized tubulin in complex with one or more nucleic acid-trapping proteins complexed bound to nucleic acid molecules susceptible to be present in the sample, wherein the nucleic acid-trapping protein(s) comprise(s) a nucleic acid-binding moiety and a polymerized tubulin-binding moiety;

b) recovering the nucleic acid-trapping protein(s) which is/are complexed bound to the nucleic acid molecules;

c) collecting the nucleic acid molecules which are bound to the nucleic acid-trapping protein(s), thereby purifying said nucleic acid molecules.

d) characterizing, preferably sequencing, the purified nucleic acid molecules.

Thus, according to said particular embodiment, the invention relates to a method for characterizing, preferably sequencing, nucleic acid molecules in a sample, comprising at least the steps of:

a) contacting said sample with at least one tubulin and one or more nucleic acid-trapping proteins comprising a nucleic acid-binding moiety and a polymerized tubulin-binding moiety, in efficient conditions for forming polymerized tubulin in complex with the said nucleic acid-trapping proteins bound to the said nucleic acids to be purified;

b) recovering the nucleic acid-trapping protein(s) which is/are bound to the nucleic acid molecules, c) collecting the nucleic acid molecules which are complexed with the nucleic acid-trapping protein(s), thereby purifying said nucleic acid molecule;

d) characterizing, preferably sequencing, the purified nucleic acid molecules.

Advantageously, any method for purifying and/or characterizing nucleic acid molecules as defined above may be considered within a method for comparing the amounts of target nucleic acid molecules between two samples; for instance for diagnosis and/or for determining the expression of a given set of nucleic acids over a reference.

Thus, according to another object, the invention relates to a method for comparing the amounts of target nucleic acid molecules between two samples comprising at least the steps of:

a) performing a method for purifying nucleic acid molecules as defined above on a first sample by using a selected nucleic acid-trapping protein, so as to obtain a first collection of purified target nucleic acid molecules, b) performing a method for purifying nucleic acid molecules as defined above on a second sample by using the same selected nucleic acid-trapping molecule as that used at step a), so as to obtain a second collection of purified target nucleic acid molecules, and c) determining the amount of target nucleic acid molecules comprised in the first collection of purified target nucleic acid molecules and in the second collection of purified target nucleic acid molecules, respectively.

Advantageously, the method for comparing the amounts of target nucleic acid molecules between two samples may further comprise a step of characterizing, preferably sequencing, the recovered and/or collected nucleic acid molecules.

A nucleic acid-trapping protein, and/or a vector comprising an expression cassette for expressing a nucleic acid-trapping protein, and/or a cell expressing a nucleic acid-trapping protein, and/or lyophilized or purified tubulin may also be considered in the form of kits for purifying nucleic acid molecules and/or for preparing an affinity support for purifying nucleic acid molecules.

Thus, according to one embodiment, the invention also relates to a kit for purifying nucleic acid molecules and/or for preparing an affinity support for purifying nucleic acid molecules, comprising:

a) at least one nucleic acid-trapping protein, and/or a vector comprising an expression cassette for expressing a nucleic acid-trapping protein, and/or a cell (preferably an eukaryotic cell) expressing a nucleic acid-trapping protein; and b) lyophilized or purified tubulin;

characterized in that the nucleic acid-trapping protein comprises a nucleic acid-binding moiety and a polymerized tubulin-binding moiety.

A vector of the invention may include one, or more than one, selectable marker. A selectable marker is a marker gene introduced into a cell, especially a bacterium or cells in culture, that confers a trait suitable for artificial selection.

According to preferred embodiments, the expression cassette is coding for a nucleic acid-trapping protein comprising a polymerized tubulin binding moiety comprising one or more Microtubule-Binding Domain (MBD) which are derived from a Microtubule-Associated Protein of the invention.

According to a most preferred embodiment, the expression cassette is coding for a polymerized-tubulin binding moiety comprising one or more Microtubule-Binding Domain (MBD) which are derived from the protein Tau of sequence: SEQ ID No 10.

Examples of vectors which are suitable for expression in eukaryotic cells include the Gateway® pEF-Dest51 plasmid.

Methods for Preparing an Affinity Support

A method for preparing an affinity support for purifying nucleic acid molecules contained in a sample, comprising an in vitro step of immobilizing one or more nucleic acid-trapping proteins on polymerized tubulin; wherein the nucleic acid-trapping protein comprises a nucleic acid-binding moiety and a polymerized tubulin-binding moiety, thereby preparing said affinity support for purifying nucleic acid molecules.

Also, at least two non mutually-exclusive alternative embodiments are envisioned herein for preparing said affinity (solid) supports, wherein:
- the one or more nucleic acid-trapping protein(s) is/are immobilized on polymerized tubulin; and/or
- the one or more nucleic acid-trapping protein(s) is/are immobilized on tubulin; under conditions suitable for tubulin polymerization.

According to one embodiment, affinity supports prepared according to said methods are further considered as part of the invention.

According to one embodiment, the invention also relates to an affinity support for purifying nucleic acid molecules comprising nucleic acid-trapping proteins immobilized on recombinant or synthetic polymerized tubulin, wherein the nucleic acid-trapping protein comprises a nucleic acid-binding moiety and a polymerized tubulin-binding moiety.

Said nucleic acid-trapping proteins may be covalently bound or non-covalently bound to the said polymerized tubulin.

According to one embodiment, the affinity support may comprise a plurality of distinct nucleic acid-trapping proteins immobilized on said recombinant or synthetic polymerized tubulin.

For example, the affinity support may comprise nucleic acid-trapping proteins immobilized on recombinant or synthetic polymerized tubulin, wherein the said polymerized tubulin is itself is immobilized on a solid support.

Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers.

In some embodiments, the solid support comprises a patterned surface suitable for immobilization. A "patterned surface" refers to an arrangement of different regions in or on an exposed layer of a solid support.

Nucleic-Acid Trapping Protein

As previously defined, a "nucleic acid-trapping protein" comprises at least one nucleic acid-binding moiety and at least one (preferably more than one) polymerized tubulin-binding moiety. The polymerized tubulin-binding moiety may comprise one or more than one Microtubule-Binding Domain(s).

The "Microtubule-Binding Domain" (MBD) relates to the one or more fragment(s) of a microtubule-binding protein that is/are responsible for its binding to polymerized tubulin, and in particular microtubules.

Although "Microtubule-Associated Proteins" (MAP) may be also polymerized-tubulin binding proteins and/or Microtubule-binding proteins, the expression "Microtubule-Binding Domain" (MBD) refers to a domain that is able to specifically and bind directly to microtubules. For the same reasons, a "polymerized-tubulin binding moiety" will refer to a moiety that binds specifically and directly to polymerized-tubulin.

Thus, a MBD may comprise all the possible sequences of amino acids that lead to the binding of the microtubule-binding protein to microtubules.

For reference, a Microtubule-Binding Domain of the invention may be derived from the Tau protein, such as the Tau isoform 2 (Accession Number: NP_005901.2), which includes sequence SEQ ID No 1, which includes sequences SEQ ID No 11 to 14.

A Microtubule-Binding Domain of the invention may also be derived from the MAP1A protein (Accession Number: NP_002364), which includes sequence SEQ ID No 2.

A Microtubule-Binding Domain of the invention may also be derived from the MAP2 protein (Accession Number: NP_002365), which includes sequence SEQ ID No 3.

A Microtubule-Binding Domain of the invention may also be derived from the MAP4 protein (Accession Number: AAA67361), which includes sequence SEQ ID No 4. A Microtubule-Binding Domain of the invention may also be derived from the MAP6 protein (Accession Number: NP_149052), which includes sequence SEQ ID No 5.

A Microtubule-Binding Domain of the invention may also be derived from the EB1 protein (Accession Number: NP_036457), which includes sequence SEQ ID No 6.

Thus, a Microtubule-Binding Domain of the invention may be selected in a group comprising: Tau of sequence SEQ ID No 1 and SEQ ID No 10 to 14, MAP1A of sequence SEQ ID No 2, MAP2 of sequence SEQ ID No 3, MAP4 of sequence SEQ ID No 4, MAP6 of sequence SEQ ID No 5, EB-1 of sequence SEQ ID No 6 and/or any Microtubule-Binding Domain that is derived from Microtubule-Associated proteins, and fragments, and combinations thereof.

Methods for identifying polymerized-tubulin binding moieties and/or microtubule-binding domains in a protein have already been reported in the Art. See for reference: Cravchik et al.; Identification of a novel microtubule-binding domain in microtubule-associated protein 1A (MAP1A). J Cell Sci, 107 (Pt 3), 661-72, 1994.

An assay for determining the sequence of putative Microtubule-Binding Domains is further provided herebelow:

The proposed procedure to test whether or not a sequence of amino acids is a "Microtubule-Binding Domain" with a Boolean answer is based on the appearance of a microtubule-like pattern by optical microscopy in cells expressing the tested amino acid sequence using direct (fluorescent tags such as GFP) or indirect labeling (antibody).

For example, spastin (accession: NP_055761), a microtubule-severing proteins, when mutated at lysine 388 to arginine (K388R) to prevent microtubule severing, binds microtubules strongly. Such sequence of amino acids can be considered as a "microtubule-binding domain". See for reference: Errico et al.; Spastin, the protein mutated in autosomal dominant hereditary spastic paraplegia, is involved in microtubule dynamics, Hum Mol Genet, 11, 153-163, 2002.

Microtubule-Binding Domains (MBP) are often found in tandems, and/or as repeats. For instance, Tau protein is a highly soluble microtubule-associated protein (MAP) for which at least six isoforms have been found in humans, and which may comprise three or four Microtubule-Binding Domains on its carboxy-terminus end.

For example, the longest tau iso form comprises four putative microtubule-binding domains (aa: 243-274; 275-305, 306-336 and 337-368. Accession NP_005901.2), respectively of sequences SEQ ID No 11-14. However the flanking regions of tau also reinforce its binding to microtubules. See for reference: Trinczek et al., Domains of tau protein, differential phosphorylation, and dynamic instability of microtubules. Mol Biol Cell, 6(12), 1887-902.

Thus, such flanking regions may also be included as an additional part of the Microtubule-Binding Domain, without departing from the scope of the invention.

The above-mentioned polymerized tubulin-binding moiety and nucleic-acid binding moieties are generally polypeptides, or fragments thereof; said polypeptides being preferably naturally-occurring polypeptides.

According to one embodiment, a nucleic-acid trapping protein may comprise a polymerized tubulin-binding moiety comprising more than one Microtubule-Binding Domain (MBD), and at least one nucleic-acid binding moiety.

According to one non-mutually exclusive embodiment, the polymerized tubulin-binding moiety comprised in a nucleic acid-trapping protein comprises one or more Microtubule Binding Domains (MBDs) present in proteins selected from the group consisting of: Tau, MAP1A, MAP2, MAP4, MAP6 and EB1.

Thus, a polymerized-tubulin binding moiety preferably comprises a plurality of Microtubule-Binding Domain(s), which includes Microtubule-Binding Domains in tandems and/or repeats, which also includes at least two, at least three, or even at least four Microtubule-Binding Domains. These domains can also be separated by linkers, in order to improve their binding to microtubules Microtubule-Binding Domains may be the same or different. In particular, they may be part of the same microtubule-binding protein, or from different microtubule-binding proteins. Preferably, they are part of the same microtubule-binding protein.

According to one exemplary embodiment, a polymerized-tubulin binding moiety includes at least one fragment of Tau that binds to microtubules, which also includes at least one Tau Microtubule-Binding Domain, such as a Tau MBD of sequence SEQ ID No 1, SEQ ID No 11, SEQ ID No 12, SEQ ID No 13 and/or SEQ ID No 14, and combinations thereof.

According to another non-mutually exclusive embodiment, the nucleic acid-binding moiety comprised in a nucleic acid-trapping protein comprises one or more nucleic acid-binding domains selected in a group consisting of: TDP43, FUS, TAF15, NF45/NF90, DDX6, hnNRP A1, DHX36, FMRP, HuD, hnRNP L, HUR, G3BP1, Lin28A, Lin28B, AGO, HuR, METTL3, METTL14, FTO, ALKBH, YTHDF1-3, PABP1 and YBX1. (Examples of RNA-binding proteins (RBPs) which are suitable for the invention are, in a non-exhaustive manner, indicated in Table 1 herebelow.

TABLE 1

Examples of RNA-binding proteins (RBPs)

| geneSymbol | gene ID | description |
|---|---|---|
| A2BP1 | 54715 | ataxin 2-binding protein 1 |
| ACO1 | 48 | aconitase 1, soluble |
| ADAT1 | 23536 | adenosine deaminase, tRNA-specific 1 |
| AKAP1 | 8165 | A kinase (PRKA) anchor protein 1 |
| APOBEC1 | 339 | apolipoprotein B mRNA editing enzyme, catalytic polypeptide 1 |
| APOBEC2 | 10930 | apolipoprotein B mRNA editing enzyme, catalytic polypeptide-like 2 |
| APOBEC3F | 200316 | apolipoprotein B mRNA editing enzyme, catalytic polypeptide-like 3F |
| APOBEC3G | 60489 | apolipoprotein B mRNA editing enzyme, catalytic polypeptide-like 3G |
| BARD1 | 580 | BRCA1 associated RING domain 1 |
| CIRBP | 1153 | cold inducible RNA binding protein |
| CPSF6 | 11052 | cleavage and polyadenylation specific factor 6, 68 kDa |
| CSDC2 | 27254 | cold shock domain containing C2, RNA binding |
| CSTF1 | 1477 | cleavage stimulation factor, 3' pre-RNA, subunit 1, 50 kDa |
| CSTF2 | 1478 | cleavage stimulation factor, 3' pre-RNA, subunit 2, 64 kDa |
| CSTF3 | 1479 | cleavage stimulation factor, 3' pre-RNA, subunit 3, 77 kDa |
| CUGBP2 | 10659 | CUG triplet repeat, RNA binding protein 2 |
| CWC15 | 51503 | CWC15 homolog (*S. cerevisiae*) |
| DAZ2 | 57055 | deleted in azoospermia 2 |
| DAZAP1 | 26528 | DAZ associated protein 1 |
| DAZL | 1618 | deleted in azoospermia-like |
| DDX17 | 10521 | DEAD (Asp-Glu-Ala-Asp) box polypeptide 17 |
| DDX19B | 11269 | DEAD (Asp-Glu-Ala-As) box polypeptide 19B |
| DDX43 | 55510 | DEAD (Asp-Glu-Ala-Asp) box polypeptide 43 |
| DKC1 | 1736 | dyskeratosis congenita 1, dyskerin |
| DUSP11 | 8446 | dual specificity phosphatase 11 (RNA/RNP complex 1-interacting) |
| DZIP3 | 9666 | DAZ interacting protein 3, zinc finger |
| EIF2S2 | 8894 | eukaryotic translation initiation factor 2, subunit 2 beta, 38 kDa |
| EIF4B | 1975 | eukaryotic translation initiation factor 4B |
| EIF4H | 7458 | eukaryotic translation initiation factor 4H |
| ELAVL4 | 1996 | ELAV (embryonic lethal, abnormal vision, *Drosophila*)-like 4 (Hu antigen D) |
| ERAL1 | 26284 | Era G-protein-like 1 (*E. coli*) |
| ETF1 | 2107 | eukaryotic translation termination factor 1 |
| EWSR1 | 2130 | Ewing sarcoma breakpoint region 1 |
| EXOSC1 | 51013 | exosome component 1 |
| EXOSC7 | 23016 | exosome component 7 |
| EXOSC9 | 5393 | exosome component 9 |
| FAU | 2197 | Finkel-Biskis-Reilly murine sarcoma virus (FBR-MuSV) ubiquitously expressed |
| FBL | 2091 | fibrillarin |
| FUS | 2521 | fusion (involved in t(12; 16) in malignant liposarcoma) |
| FXR1 | 8087 | fragile X mental retardation, autosomal homolog 1 |
| FXR2 | 9513 | fragile X mental retardation, autosomal homolog 2 |
| G3BP2 | 9908 | GTPase activating protein (SH3 domain) binding protein 2 |
| HNRNPA0 | 10949 | heterogeneous nuclear ribonucleoprotein A0 |
| HNRNPA2B1 | 3181 | heterogeneous nuclear ribonucleoprotein A2/B1 |
| HNRNPC | 3183 | heterogeneous nuclear ribonucleoprotein C (C1/C2) |
| HNRNPL | 3191 | heterogeneous nuclear ribonucleoprotein L |

TABLE 1-continued

Examples of RNA-binding proteins (RBPs)

| geneSymbol | gene ID | description |
| --- | --- | --- |
| HNRNPR | 10236 | heterogeneous nuclear ribonucleoprotein R |
| HNRNPU | 3192 | heterogeneous nuclear ribonucleoprotein U (scaffold attachment factor A) |
| HNRPA3 | 220988 | heterogeneous nuclear ribonucleoprotein A3 |
| HNRPD | 3184 | heterogeneous nuclear ribonucleoprotein D |
| HNRPF | 3185 | heterogeneous nuclear ribonucleoprotein F |
| HNRPH2 | 3188 | heterogeneous nuclear ribonucleoprotein H2 (H') |
| HNRPH3 | 3189 | heterogeneous nuclear ribonucleoprotein H3 (2H9) |
| HNRPK | 3190 | heterogeneous nuclear ribonucleoprotein K |
| HNRPM | 4670 | heterogeneous nuclear ribonucleoprotein M |
| HNRPUL1 | 11100 | heterogeneous nuclear ribonucleoprotein U-like 1 |
| HRB | 3267 | HIV-1 Rev binding protein |
| HSP90B1 | 7184 | heat shock protein 90 kDa beta (Grp94), member 1 |
| IGF2BP2 | 10644 | insulin-like growth factor 2 mRNA binding protein 2 |
| IGF2BP3 | 10643 | insulin-like growth factor 2 mRNA binding protein 3 |
| IREB2 | 3658 | iron-responsive element binding protein 2 |
| JAKMIP1 | 152789 | janus kinase and microtubule interacting protein 1 |
| KHDRBS1 | 10657 | KH domain containing, RNA binding, signal transduction associated 1 |
| KIAA1604 | 57703 | KIAA1604 protein |
| KIN | 22944 | KIN, antigenic determinant of recA protein homolog (mouse) |
| LRPPRC | 10128 | leucine-rich PPR-motif containing |
| LSM5 | 23658 | LSM5 homolog, U6 small nuclear RNA associated (S. cerevisiae) |
| MKI67IP | 84365 | MKI67 (FELA domain) interacting nucleolar phosphoprotein |
| MOV10L1 | 54456 | Mov10l1, Moloney leukemia virus 10-like 1, homolog (mouse) |
| MRPL12 | 6182 | mitochondrial ribosomal protein L12 |
| MRPL23 | 6150 | mitochondrial ribosomal protein L23 |
| MRPL3 | 11222 | mitochondrial ribosomal protein L3 |
| MRPS7 | 51081 | mitochondrial ribosomal protein S7 |
| MSI1 | 4440 | musashi homolog 1 (Drosophila) |
| NCL | 4691 | nucleolin |
| NHP2L1 | 4809 | NHP2 non-histone chromosome protein 2-like 1 (S. cerevisiae) |
| NOL3 | 8996 | nucleolar protein 3 (apoptosis repressor with CARD domain) |
| NOL4 | 8715 | nucleolar protein 4 |
| NOL5A | 10528 | nucleolar protein 5A (56 kDa with KKE/D repeat) |
| NOVA1 | 4857 | neuro-oncological ventral antigen 1 |
| NOVA2 | 4858 | neuro-oncological ventral antigen 2 |
| NPM1 | 4869 | nucleophosmin (nucleolar phosphoprotein B23, numatrin) |
| NR0B1 | 190 | nuclear receptor subfamily 0, group B, member 1 |
| NUDT21 | 11051 | nudix (nucleoside diphosphate linked moiety X)-type motif 21 |
| NUFIP1 | 26747 | nuclear fragile X mental retardation protein interacting protein 1 |
| NUFIP2 | 57532 | nuclear fragile X mental retardation protein interacting protein 2 |
| NXF2 | 56001 | nuclear RNA export factor 2 |
| NXF5 | 55998 | nuclear RNA export factor 5 |
| PABPN1 | 8106 | poly(A) binding protein, nuclear 1 |
| PAIP1 | 10605 | poly(A) binding protein interacting protein 1 |
| PAPOLA | 10914 | poly(A) polymerase alpha |
| PCBP1 | 5093 | poly(rC) binding protein 1 |
| PCBP2 | 5094 | poly(rC) binding protein 2 |
| PCBP3 | 54039 | poly(rC) binding protein 3 |
| PCBP4 | 57060 | poly(rC) binding protein 4 |
| PCBP4 | 57060 | poly(rC) binding protein 4 |
| POP4 | 10775 | processing of precursor 4, ribonuclease P/MRP subunit (S. cerevisiae) |
| PPARGC1A | 10891 | peroxisome proliferator-activated receptor gamma, coactivator 1 alpha |
| PPARGC1B | 133522 | peroxisome proliferator-activated receptor gamma, coactivator 1 beta |
| PPIE | 10450 | peptidylprolyl isomerase E (cyclophilin E) |
| PPP1R8 | 5511 | protein phosphatase 1, regulatory (inhibitor) subunit 8 |
| PSMA1 | 5682 | proteasome (prosome, macropain) subunit, alpha type, 1 |
| PSMA6 | 5687 | proteasome (prosome, macropain) subunit, alpha type, 6 |
| RAD51AP1 | 10635 | RAD51 associated protein 1 |
| RAE1 | 8480 | RAE1 RNA export 1 homolog (S. pombe) |
| RALY | 22913 | RNA binding protein, autoantigenic (hnRNP-associated with lethal yellow homolog (mouse)) |
| RBM10 | 8241 | RNA binding motif protein 10 |
| RBM14 | 10432 | RNA binding motif protein 14 |
| RBM3 | 5935 | RNA binding motif (RNP1, RRM) protein 3 |
| RBM4 | 5936 | RNA binding motif protein 4 |
| RBM45 | 129831 | RNA binding motif protein 45 |
| RBM5 | 10181 | RNA binding motif protein 5 |
| RBM6 | 10180 | RNA binding motif protein 6 |
| RBM9 | 23543 | RNA binding motif protein 9 |
| RBMS1 | 5937 | RNA binding motif, single stranded interacting protein 1 |
| RBMS2 | 5939 | RNA binding motif, single stranded interacting protein 2 |
| RBMX | 27316 | RNA binding motif protein, X-linked |
| RBMY1A1 | 5940 | RNA binding motif protein, Y-linked, family 1, member A1 |
| RBPMS | 11030 | RNA binding protein with multiple splicing |
| RCAN3 | 11123 | RCAN family member 3 |
| RDBP | 7936 | RD RNA binding protein |

TABLE 1-continued

Examples of RNA-binding proteins (RBPs)

| geneSymbol | gene ID | description |
| --- | --- | --- |
| RNASE1 | 6035 | ribonuclease, RNase A family, 1 (pancreatic) |
| RNASEH1 | 246243 | ribonuclease H1 |
| RNASEL | 6041 | ribonuclease L (2',5'-oligoisoadenylate synthetase-dependent) |
| RNMT | 8731 | RNA (guanine-7-) methyltransferase |
| RNPS1 | 10921 | RNA binding protein S1, serine-rich domain |
| RNU2 | 6066 | RNA, U2 small nuclear |
| ROD1 | 9991 | ROD1 regulator of differentiation 1 (*S. pombe*) |
| RPL13 | 6137 | ribosomal protein L13 |
| RPL14 | 9045 | ribosomal protein L14 |
| RPL15 | 6138 | ribosomal protein L15 |
| RPL17 | 6139 | ribosomal protein L17 |
| RPL18 | 6141 | ribosomal protein L18 |
| RPL18A | 6142 | ribosomal protein L18a |
| RPL19 | 6143 | ribosomal protein L19 |
| RPL21 | 6144 | ribosomal protein L21 |
| RPL22 | 6146 | ribosomal protein L22 |
| RPL24 | 6152 | ribosomal protein L24 |
| RPL26 | 6154 | ribosomal protein L26 |
| RPL27A | 6157 | ribosomal protein L27a |
| RPL28 | 6158 | ribosomal protein L28 |
| RPL29 | 6159 | ribosomal protein L29 |
| RPL3 | 6122 | ribosomal protein L3 |
| RPL30 | 6156 | ribosomal protein L30 |
| RPL31 | 6160 | ribosomal protein L31 |
| RPL34 | 6164 | ribosomal protein L34 |
| RPL38 | 6169 | ribosomal protein L38 |
| RPL39 | 6170 | ribosomal protein L39 |
| RPL3L | 6123 | ribosomal protein L3-like |
| RPL4 | 6124 | ribosomal protein L4 |
| RPL41 | 6171 | ribosomal protein L41 |
| RPL6 | 6128 | ribosomal protein L6 |
| RPL7 | 6129 | ribosomal protein L7 |
| RPL7A | 6130 | ribosomal protein L7a |
| RPL9 | 6133 | ribosomal protein L9 |
| RPLP0 | 6175 | ribosomal protein, large, P0 |
| RPLP1 | 6176 | ribosomal protein, large, P1 |
| RPLP2 | 6181 | ribosomal protein, large, P2 |
| RPN1 | 6184 | ribophorin I |
| RPP14 | 11102 | ribonuclease P/MRP 14 kDa subunit |
| RPS10 | 6204 | ribosomal protein S10 |
| RPS12 | 6206 | ribosomal protein S12 |
| RPS13 | 6207 | ribosomal protein S13 |
| RPS14 | 6208 | ribosomal protein S14 |
| RPS15A | 6210 | ribosomal protein S15a |
| RPS17 | 6218 | ribosomal protein S17 |
| RPS19 | 6223 | ribosomal protein S19 |
| RPS2 | 6187 | ribosomal protein S2 |
| RPS20 | 6224 | ribosomal protein S20 |
| RPS21 | 6227 | ribosomal protein S21 |
| RPS23 | 6228 | ribosomal protein S23 |
| RPS24 | 6229 | ribosomal protein S24 |
| RPS25 | 6230 | ribosomal protein S25 |
| RPS26 | 6231 | ribosomal protein S26 |
| RPS27 | 6232 | ribosomal protein S27 (metallopanstimulin 1) |
| RPS29 | 6235 | ribosomal protein S29 |
| RPS3 | 6188 | ribosomal protein S3 |
| RPS3A | 6189 | ribosomal protein S3A |
| RPS5 | 6193 | ribosomal protein S5 |
| RPS6 | 6194 | ribosomal protein S6 |
| RPS7 | 6201 | ribosomal protein S7 |
| RPS8 | 6202 | ribosomal protein S8 |
| RTCD1 | 8634 | RNA terminal phosphate cyclase domain 1 |
| SARS | 6301 | seryl-tRNA synthetase |
| SF1 | 7536 | splicing factor 1 |
| SFRS3 | 6428 | splicing factor, arginine/serine-rich 3 |
| SNRP70 | 6625 | small nuclear ribonucleoprotein 70 kDa polypeptide (RNP antigen) |
| SNRPD1 | 6632 | small nuclear ribonucleoprotein D1 polypeptide 16 kDa |
| SRRP35 | 135295 | serine-arginine repressor protein (35 kDa) |
| SUPV3L1 | 6832 | suppressor of var1, 3-like 1 (*S. cerevisiae*) |
| SURF6 | 6838 | surfeit 6 |
| SYNCRIP | 10492 | synaptotagmin binding, cytoplasmic RNA interacting protein |
| TARBP1 | 6894 | TAR (HIV-1) RNA binding protein 1 |
| TEP1 | 7011 | telomerase-associated protein 1 |
| TIAL1 | 7073 | TIA1 cytotoxic granule-associated RNA binding protein-like 1 |
| TROVE2 | 6738 | TROVE domain family, member 2 |
| UPF1 | 5976 | UPF1 regulator of nonsense transcripts homolog (yeast) |

TABLE 1-continued

Examples of RNA-binding proteins (RBPs)

| geneSymbol | gene ID | description |
|---|---|---|
| YBX1 | 4904 | Y box binding protein 1 |
| ZNF239 | 8187 | zinc finger protein 239 |
| ZNF638 | 27332 | zinc finger protein 638 |
| ZRANB2 | 9406 | zinc finger, RAN-binding domain containing 2 |

Functional homologs of the above-mentioned nucleic acid-binding moieties and polymerized tubulin-binding moieties are also considered, which includes polypeptides having a sequence identity of at least 20% amino acid identity with the reference sequence.

As used herein, polypeptide sequences having at least 20% amino acid identity with a reference sequence encompass those having at least 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 28%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference sequence.

Within the scope of the present invention, the "percentage identity" between two polypeptides means the percentage of identical amino acids residues between the two polypeptide sequences to be compared, obtained after optimal alignment, this percentage being purely statistical and the differences between the two polypeptide sequences being distributed randomly along their length. The comparison of two polypeptide sequences is traditionally carried out by comparing the sequences after having optimally aligned them, said comparison being able to be conducted by segment or by using an "alignment window". Optimal alignment of the sequences for comparison is carried out, by using the comparison software BLAST-P).

In its principle, the percentage identity between two amino acid sequences is determined by comparing the two optimally-aligned sequences in which the nucleic acid sequence to compare can have additions or deletions compared to the reference sequence for optimal alignment between the two polypeptide sequences. Percentage identity is calculated by determining the number of positions at which the amino acid residue is identical between the two sequences, preferably between the two complete sequences, dividing the number of identical positions by the total number of positions in the alignment window and multiplying the result by 100 to obtain the percentage identity between the two sequences.

All possible combinations of nucleic acid-binding moieties and polymerized tubulin-binding moieties are also clearly envisioned.

A barrier for interaction can be a reduction of the accessibility of the nucleic-acid binding moiety when fused to a polymerized tubulin-binding moiety due to the proximity of the polymerized tubulin surface. To maximize the nucleic acid-binding moiety's accessibility to the nucleic acid to be purified in the sample, the bait can be attached to a projection domain, which is preferably an unstructured tail allowing a nm-long spacing between the microtubule or the polymerized-tubulin surface and the nucleic acid.

Accordingly, the nucleic-acid trapping protein may further comprise one Linker (L) region located between the nucleic acid-binding moiety and the polymerized tubulin-binding moiety. A Linker (L) region is generally an unstructured domain, in particular an unstructured domain which allows a nm-long spacing between the polymerized-tubulin surface and the nucleic acid of interest, which is critical to increase the accessibility of the nucleic acid binding moiety and the polymerized tubulin-binding moiety. Examples of Linker regions are known in the Art.

Projection domains are found in Microtubule-Associated Proteins (MAPs) such as MAP2 or Tau, and are involved in microtubule bundling and in determining the spacing between microtubules.

Preferably, in order to maximize the nucleic acid binding moiety's accessibility to the nucleic acid, the nucleic acid binding moiety is attached to a Linker region which is a projection domain from a MAP, such as Tau, or a fragment thereof.

A "projection domain" of the invention may comprise or consist of a N-terminal fragment of Tau.

According to a particular embodiment, a "projection domain" of the invention is the Tau projection domain of sequence, SEQ ID No 9, or a fragment thereof.

The Linker region, or projection domain, can be of varying length, which includes any region or domain as defined above of from 1 to 150 amino acids in length, which includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 and 150 amino acids in length.

When the nucleic acid-trapping protein comprises (i) a polymerized-tubulin binding moiety comprising one or more Microtubule-Binding Domains and (ii) a projection domain, it is preferable that both parts are part of the same protein, in particular the same Microtubule-Associated Protein, such as Tau.

The nucleic acid-trapping protein moiety may or may not comprise a detectable moiety, such a fluorescent protein.

Advantageously, the nucleic acid-trapping protein may further comprise any detectable moiety as defined above, at its N-terminal or C-terminal part, such as a fluorescent label that is detectable using fluorescence microscopy.

In a non-limitative manner, the detectable moiety may be a fluorescent protein, such as a protein selected in a group comprising: GFP, YFP, XFP, RFP, CFP, DsRED, and mCherry.

EXAMPLES

A. Material & Methods

A1.1) Preparation of Plasmids Encoding for Tau-RBPs

Vectors leading the mammalian expressions of tau-RFP-RBPs and tau-GFP-RBPs were engineered using the gateway strategy as previously described in (Boca et al. Probing protein interactions in living mammalian cells on a microtubule bench. Scientific reports 5, 17304 (2015)).

The human sequences of following RBPs were inserted: TDP-43, G3BP1, HuR, FUS, YB-1, Lin28a. The tau-RFP-TDP-43 constructs (TDP-43ΔRBD, 270-414 aa; and TDP-43ΔLCD, 1-277 aa) were amplified by PCR using primers containing PacI and AscI restriction sites and cloned into the "backbone entry plasmid" containing RFP-Tau cassette. The two TDP (1-277aa or 270-414aa)-RFP-Tau cassettes were then transferred into the pDEST expression vector using the LR reaction (see table 2).

TABLE 2

| Plasmids | Expression vectors | RBP accession numbers |
| --- | --- | --- |
| Tau-RFP-TDP43 | PEF-DEST51 | NP_031401.1 |
| Tau-RFP-FUS | PEF-DEST51 | NP_004951.1 |
| Tau-RFP-YB1 | PEF-DEST51 | NP_004550.2 |
| Tau-RFP-HUR | PEF-DEST51 | NP_001410 |
| Tau-RFP-G3BP1 | PEF-DEST51 | NP_005745.1 |
| Tau-RFP-Lin28A | PEF-DEST51 | NP_078950.1 |
| Tau-GFP-TDP43 | PEF-DEST51 | NP_031401.1 |
| Tau-GFP-YB1 | PEF-DEST51 | NP_004550.2 |
| Tau-GFP-G3BP1 | PEF-DEST51 | NP_005745.1 |
| GFP-YB1 | pEGFP-C3 | NP_004550.2 |
| GFP-HUR | pEGFP-C3 | NP_001410 |

A2. Nucleic Acid Purification Followed by RT-PCR Analysis $10^6$ HEK 293T cells (Source: ATCC; Identifier: CRL-3216) were plated in 6-well plates and transfected with tau-RFP-RBPs expression plasmids with Lipofectamine 2000™ reagent (Invitrogen). 24 hours after transfection, cells were placed on ice for 30 min and lysed in 200 µL of lysis buffer (50 mM TrisHCl [pH 7.0], 50 mM NaCl, 1 mM EDTA, 0.05% sodium deoxycholate, 1% Triton X-100, 0.1% SDS, 1 mM PMSF, protease and RNAse inhibitors). Tubulin was purified from sheep brain.

Tubulin concentration was determined by spectrophotometry using an extinction coefficient of 1.2 $mg^{-1} \times cm^2$ at 278 nm. Tubulin polymerization was initiated by placing the ice-cold cuvette (1 cm light path) at 37° C. in a PTI QuantaMaster 2000-4 thermostated spectrofluorimeter. The kinetics of microtubule assembly were then immediately monitored by 90° light scattering at 370 nm. Microtubules were then taxol-stabilized (5 µM taxol, 40 µM tubulin).

Cell lysates were centrifuged at 20,000×g for 1 h at 16° C. and the supernatant was collected. 10 µL of microtubule solution was added to 200 µl of cell supernatant, incubated for 15 min at 16° C. and centrifuged at 20,000×g for 30 min at 16° C. The microtubule pellet was resuspended in 100 µL of lysis buffer and again centrifuged at 20,000×g for 30 min. After discarding the supernatant, RNA was purified from the pellet with Tri-Reagent (Molecular Research Center, Inc.)) RNA quality was assessed by UV-spectrometry (nanodrop). RT-PCR reactions were performed using impromII Reverse transcriptase and GoTaq® qPCR Master Mix on a 7500 Applied Biosytems™ block. RNA quantification results obtained with the microtubule pellet were compared to those obtained from the whole cell lysate.

For classical IP analysis, HEK cells expressing indicated GFP-RBPs we lysed under conditions mentioned above. The co-immunoprecipitation assays were performed using Dynabeads® Protein G Kit (Invitrogen) in the same buffer used to isolate RNA in a microtubule pellet, except the incubation time (here overnight in a cold room). RT-PCR analysis was performed as described above.

B. Results

To confine HuR, G3BP1 and YB-1 on microtubules, they were fused to tau (FIG. 1A), a microtubule-associated protein, and an RFP or GFP label. The proteins are fusion are thus the nucleic acid-trapping protein(s) that bring mRNA onto microtubules. Tau has a higher affinity for polymerized than for free tubulin which favors its presence onto microtubules rather than in the cytosol. In addition, its unstructured N-terminus serves as a spacer to preserve protein functions. To purify RNA molecules which are complexed with the nucleic acid-trapping protein(s), we reasoned that RNA brought onto microtubules could be isolated from cell lysates in vitro. To this end, lysate of cells lysates of cells expressing nucleic acid-trapping protein(s) were centrifuged at 20,000×g for 1 h at 16° C. and the supernatant was collected. Then the supernatant were incubated with sheep brain microtubules (FIG. 1B) and centrifuged at 20,000×g for 30 min at 16° C. Alternatively, the supernatant could be incubated under conditions favorable for the polymerization of endogenous tubulin or after the addition of exogenous tubulin (FIG. 1C) and then centrifuged at 20,000×g for 30 min at 16° C.

Figure 1B:
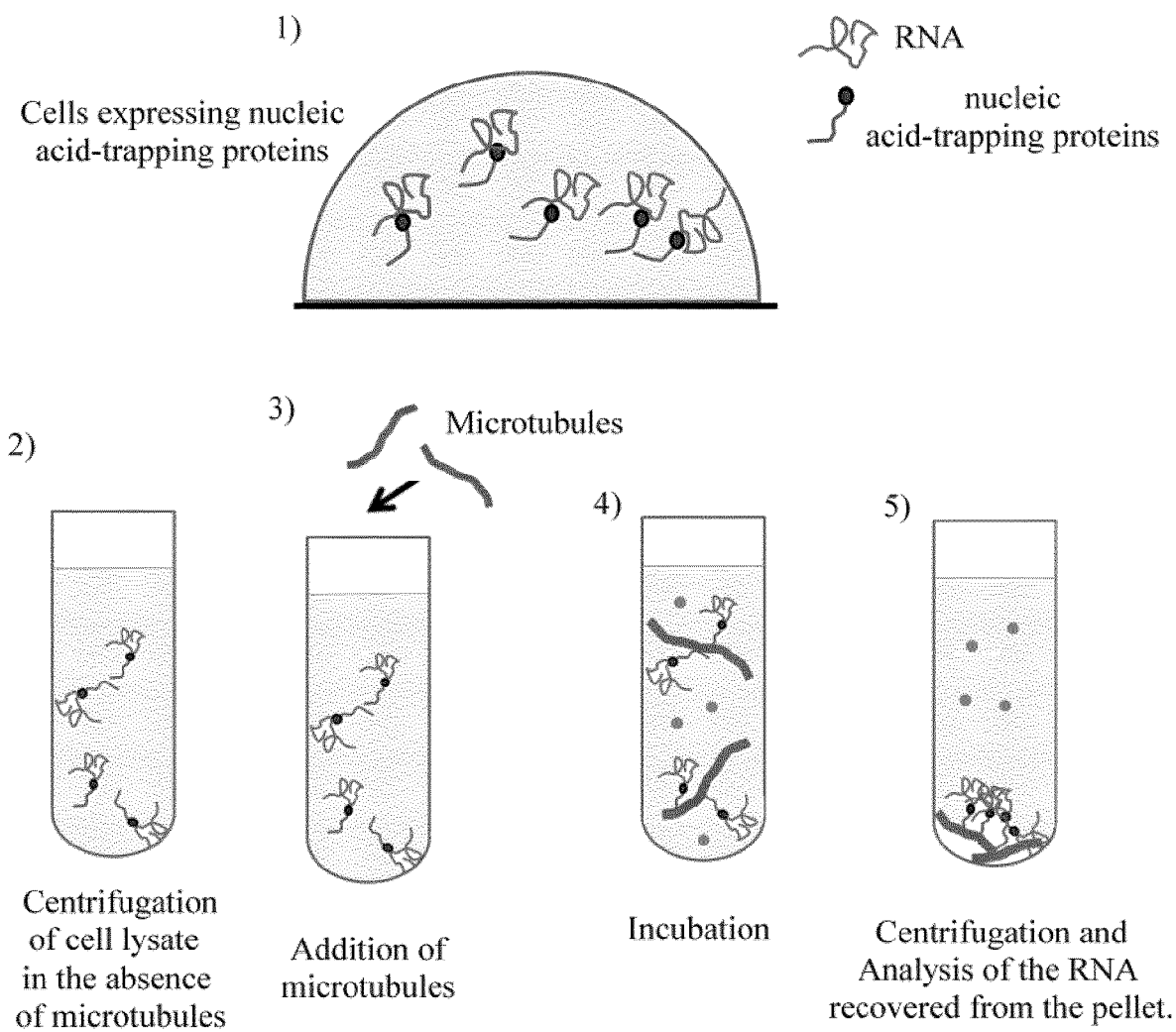
Figure 1C:
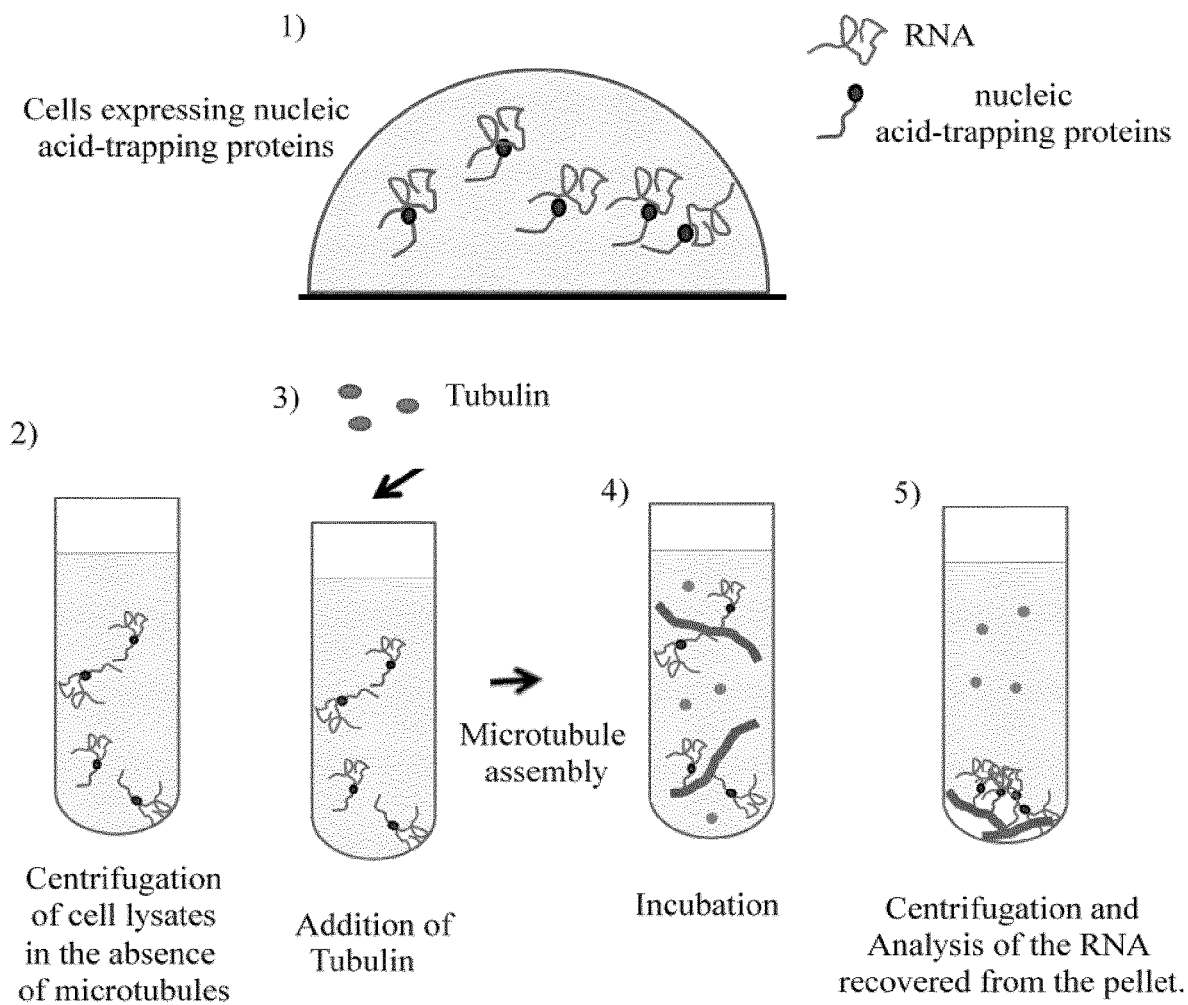
Figure 2A:
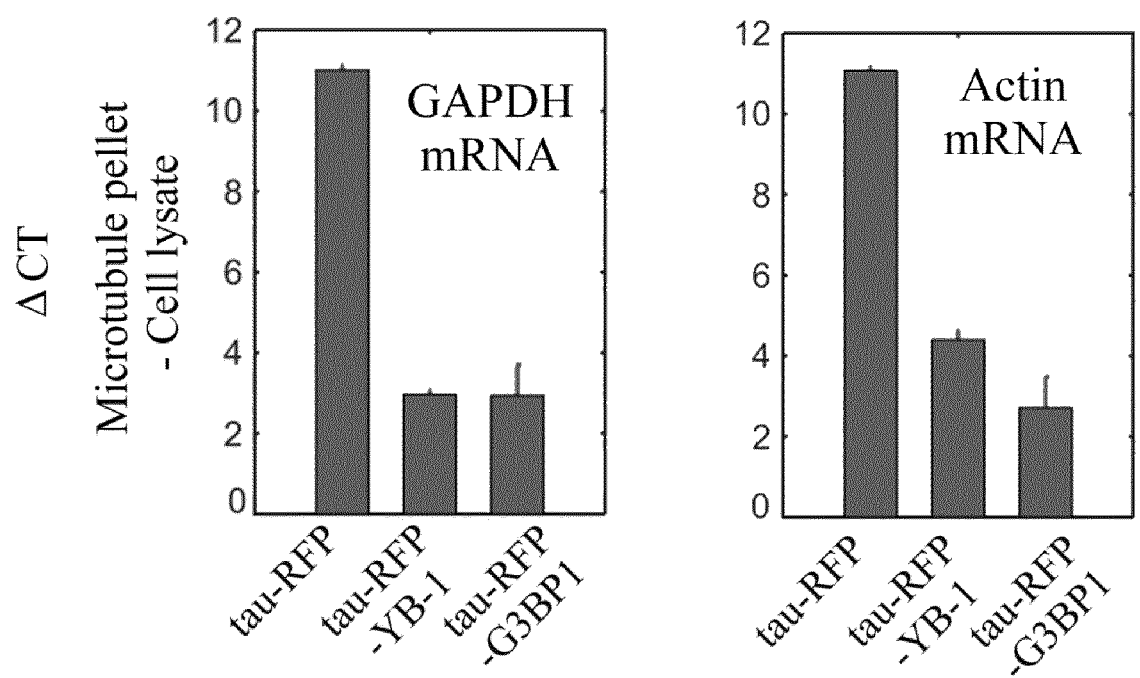
FIG. 2: Analysis of the binding of tau-RBP to microtubules. A. RT-PCR analysis of the presence of GAPDH and actin mRNAs isolated in microtubule pellets from HEK293T cells expressing indicated constructs. For comparison, the CT values from the microtubule pellets were subtracted to those obtained in whole cell lysate before centrifugation. CT, Cycle Threshold. Reported values are the means±SD (n=3). The y-axis is expressed as a ΔCT [microtubule pellet—cell lysate]. B & C. RT-PCR analysis of mRNAs isolated in the microtubule pellet from HEK293T cells expressing indicated tau-GFP-RBPs (upper-panel) or via anti-GFP immunoprecipitation (IP) (down panel) from cells expressing GFP-RBPs. The y-axis is expressed as a $Log_2$ enrichment.

The ribonucleoproteins (RNP) interacting with microtubules were purified according to the protocol described in FIG. 1B and the mRNA content of the pellet analyzed by RT-PCR. The amount of mRNA found in these microtubule pellets increases dramatically in the presence of tau-RFP-RBP fusion in contrast to tau-RFP alone. RT-PCR analysis was performed over tens of mRNAs including those encoding for GAPDH and actin as abundant mRNA controls. As control, we detected a lower amount of mRNA from cell lysates of cells expressing Tau-RFP alone. In contrast, in cells expressing Tau-RFP-YB-1 or Tau-RFP-G3BP1, the amount of mRNA significantly increases (Lower CT values, FIG. 2A).

Figure 2B:
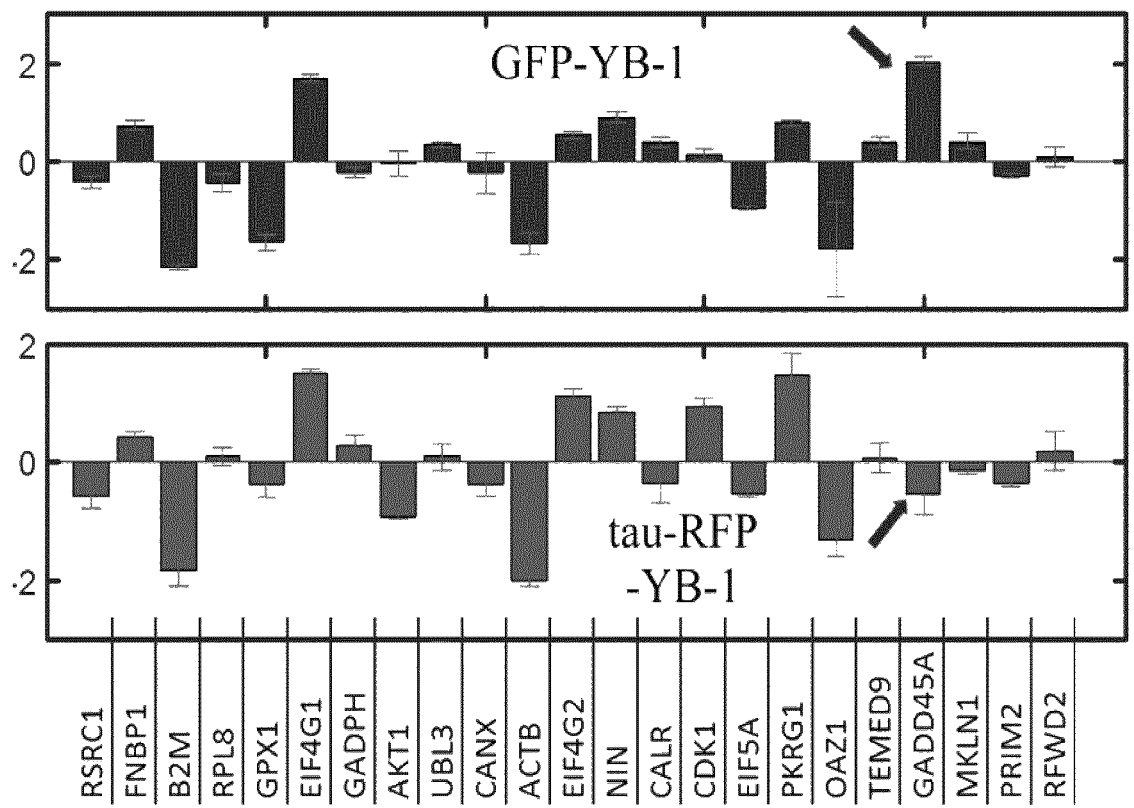
Figure 2C:
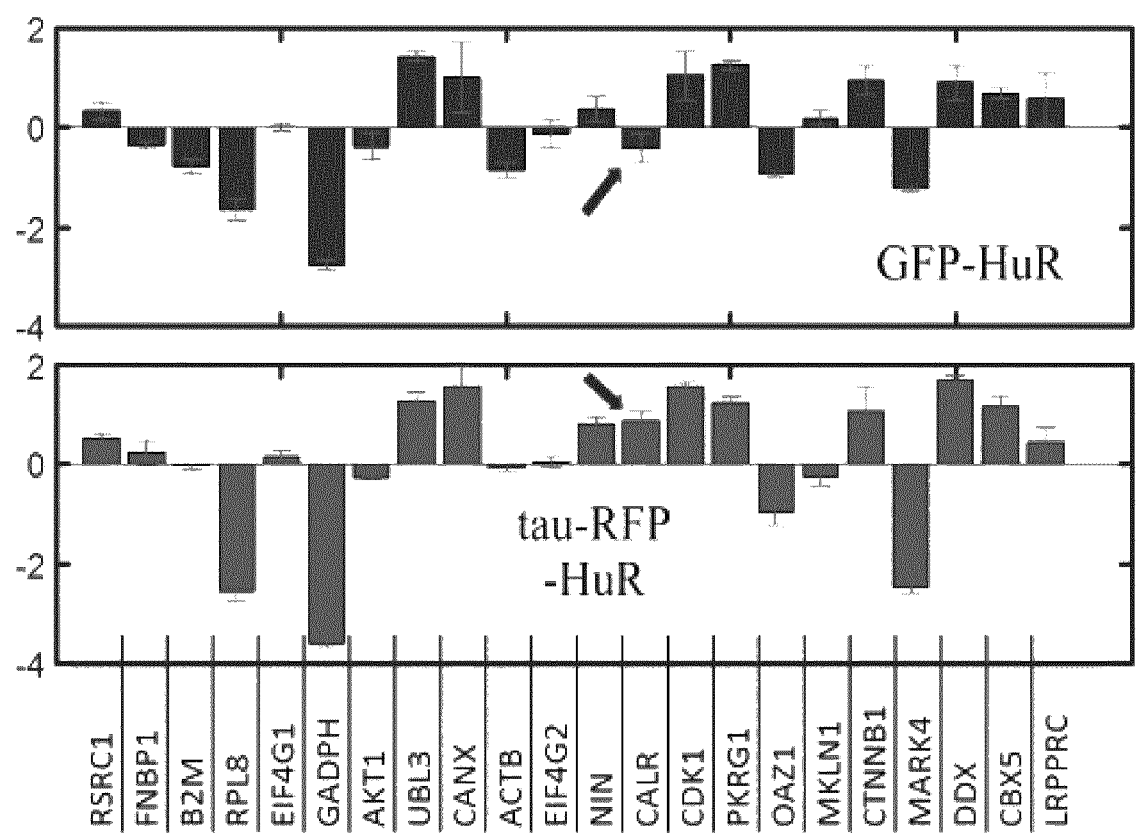

In addition, Tau-RFP-YB-1 or Tau-RFP-HuR preferentially bind to specific mRNAs, which may reflect preserved specificities. To further explore this point, we compared these enrichments to those obtained by classical immunoprecipitations with an anti-GFP antibody from cells expressing GFP-RBP. Quantification revealed similar profiles for the two methods for both HuR and YB-1, despite some discrepancies (FIGS. 2B and C). We could therefore reasonably assume that the binding of RBPs to mRNA and its specificity are globally preserved despite tau fusion and the vicinity of microtubules.

Figure 3:
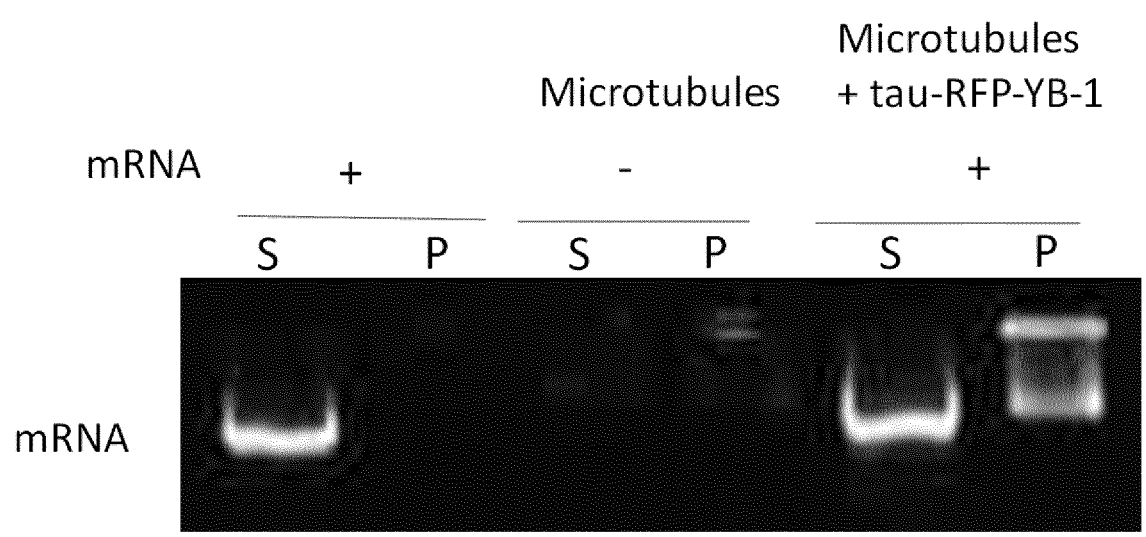
FIG. 3: Purified tau-RFP-YB-1 can be used as a protein bait to purify mRNA. Agarose gel corresponding to the content of each fraction after co-sedimentation of tau-RFP-YB-1 with microtubules on the right lanes. Controls without tau-RFP-YB1 or microtubules are respectively shown on the left and center lanes. In the upper part, the "S" stands for the supernatant fraction and the "P" stands for the pellet fraction.

Also, FIG. 3 illustrates a Tau-RFP-YB-1 construct which was expressed in HEK 293 cells and purified through co-sedimentation with microtubules at 20,000×g for 30 min at 16° C. Tau-RFP-YB-1 was suspended and treated with RNAse to remove cellular RNA. RNAse was removed after co-sedimentation of tau-RFP-YB-1 with microtubules. Finally, purified tau-RFP-YB-1 was used to capture mRNA (here synthetic Luciferase mRNA) after co-sedimentation with microtubules. This results demonstrates that purification of a tau-RFP-YB-1 construct does not impair its capacity to bind to mRNA in vitro and to co-sediment with microtubules.

SEQUENCE LISTING

SEQ ID No 1. Tau microtubule binding sequence: 151-400, Accession: NP 005901.2):
IATPRGAAPPGQKGQANATRIPAKTPPAPKTPPSSGEPPKSGDRSGYSSPG
SPGTPGSRSRTPSLPTPPTREPKKVAVVRTPPKSPSSAKSRLQTAPVPMPD
LKNVKSKIGSTENLKHQPGGGKVQIINKKLDLSNVQSKCGSKDNIKHVPGG
GSVQIVYKPVDLSKVTSKCGSLGNIHHKPGGGQVEVKSEKLDFKDRVQSKI
GSLDNITHVPGGGNKKIETHKLTFRENAKAKTDHGAEIVYKSPVVS SEQ ID No 2. MAP1A (aa: 282-630, Accession: NP 002364):
QNKILEGLEKLRHLDFLRYPVATQKDLASGAVPTNLKPSKIKQRADSKESL
KATTKTAVSKLAKREEVVEEGAKEARSELAKELAKTEKKAKESSEKPPEKP
AKPERVKTESSEALKAEKRKLIKDKVGKKHLKEKISKLEEKKDKEKKEIKK
ERKELKKDEGRKEEKKDAKKEEKRKDTKPELKKISKPDLKPFTPEVRKTLY
KAKVPGRVKIDRSRAIRGEKELSSEPQTPPAQKGTVPLPTISGHRELVLSS
PEDLTQDFEEMKREERALLAEQRDTGLGDKPFPLDTAEEGPPSTAIQGTPP
SVPGLGQEEHVMKEKELVPEVPEEQGSKDRGLDSGAETEEEKDTWEEKKQR
E SEQ ID No 3. MAP2 (aa: 1519-1828, Accession: NP 002365):
FKQAKDKVSDGVTKSPEKRSSLPRPSSILPPRRGVSGDRDENSFSLNSSIS
SSARRTTRSEPIRRAGKSGTSTPTTPGSTAITPGTPPSYSSRTPGTPGTPS
YPRTPHTPGTPKSAILVPSEKKVAIIRTPPKSPATPKQLRLINQPLPDLK
VKSKIGSTDNIKYQPKGGQVQIVTKKIDLSHVTSKCGSLKNIRHRPGGGRV
KIESVKLDFKEKAQAKVGSLDNAHHVPGGGNVKIDSQKLNFREHAKARVDH
GAEIITQSPGRSSVASPRRLSNVSSSGSINLLESPQLATLAEDVTAALAKQ
GL SEQ ID No 4. MAP4 (aa: 923-1084, Accession: AAA67361):
LATNTSAPDLKNVRSKVGSTENIKHQPGGGRAKVEKKTEAAATTRKPESNA
VTKTAGPIASAQKPGAGKVQIVSKKVSYSHIQSKCGSKDNIKHVPGGGNVQ
IQNKKVDISKVSSKCGSKANIKHKPGGGDVKIESQKLNFKEKAQAKVGSLD
NVGHLPAGG SEQ ID No 5. MAP6 (aa: 118-321, Accession: NP 149052):
SVMRQDYRAWKVQRPEPSCRPRSEYQPSDAPFERETQYKDFRAWPLPRRG
DHPWIPKPVQISAASQASAPILGAPKRRPQSQERWPVQAAAEAREQEAAPG
GAGGLAAGKASGADERDTRRKAGPAWIVRRAEGLGHEQTPLPAAQAQVQAT
GPEAGRGRAAADALNRQIREEVASAVSSSYRNEFRAWTDIKPVKPIKAKP SEQ ID No 6. EB1 (aa: 124-268, Accession: NP 036457):
YDPVAARQGQETAVAPSLVAPALNKPKKPLTSSSAAPQRPISTQRTAAAPK
AGPGVVRKNPGVGNGDDEAAELMQQVNVLKLTVEDLEKERDPYFGKLRNIE
LICQENEGENDPVLQRIVDILYATDEGFVIPDEGGPQEEQEEY SEQ ID No 7. Alpha tubulin (Accession: AAA91576):
MRECISIHVGQAGVQIGNACWELYCLEHGIQPDGQMPSDKTIGGGDDSFNT
FFSETGAGKHVPRAVFVDLEPTVIDEVRTGTYRQLFHPEQLITGKEDAANN
YARGHYTIGKEIIDLVLDRIRKLADQCTRLQGFLVFHSFGGGTGSGFTSLL
MERLSVDYGKKSKLEFSIYPAPQVSTAVVEPYNSILTTHTTLEHSDCAFMV
DNEAIYDICRRNLDIERPTYTNLNRLISQIVSSITASLRFDGALNVDLTEF
QTNLVPYPRIHFPLATYAPVISAEKAYHEQLSVADITNACFEPANQMVKCD
PGHGKYMACCLLYRGDVVPKDVNAAIATIKTKRTIQFVDWCPTGFKVGINY
QPPTVVPGGDLAKVQRAVCMLSNTTAIAEAWARLDHKFDLMYAKRAFVHWY
VGEGMEEGEFSEAREDMAALEKDYEEVGVDSVEGEGEEGEEY SEQ ID No 8. Beta tubulin (aa: 124-268, Accession: AAB59507):
MREIVHIQAGQCGNQIGAKFWEVISDEHGIDPTGTYHGDSDLQLDRISVYY
NEATGGKYVPRAILVDLEPGTMDSVRSGPFGQIFRPDNFVFGQSGAGNNWA
KGHYTEGAELVDSVLDVVRKEAESCDCLQGFQLTHSLGGGTGSGMGTLLIS
KIREEYPDRIMNTFSVVPSPKVSDTVVEPYNATLSVHQLVENTDETYCIDN
EALYDICFRTLRLTTPTYGDLNHLVSGTMECVTTCLRFPGQLNADLRKLAV
NMVPFPRLHFFMPGFAPLTSRGSQQYRALTVPDLTQQVFDAKNMMAACDPR
HGRYLTVAAVFRGRMSMKEVDEQMLNVQNKNSSYFVEWIPNNVKTAVCDIP
PRGLKMAVTFIGNSTAIQELFKRISEQFTAMFRRKAFLHWYTGEGMDEMEF
TEAESNMNDLVSEYQQYQDATAEEEEDFGEEAEEEA SEQ ID No 9. Tau projection domain (aa: 1-150, Accession: NP 005901.2):
MAEPRQEFEVMEDHAGTYGLGDRKDQGGYTMHQDQEGDTDAGLKESPLQTP
TEDGSEEPGSETSDAKSTPTAEDVTAPLVDEGAPGKQAAAQPHTEIPEGTT
AEEAGIGDTPSLEDEAAGHVTQARMVSKSKDGTGSDDKKAKGADGKTK SEQ ID No 10. Tau (Accession: NP 005901.2):
MAEPRQEFEVMEDHAGTYGLGDRKDQGGYTMHQDQEGDTDAGLKESPLQTP
TEDGSEEPGSETSDAKSTPTAEDVTAPLVDEGAPGKQAAAQPHTEIPEGTT
AEEAGIGDTPSLEDEAAGHVTQARMVSKSKDGTGSDDKKAKGADGKTKIAT
PRGAAPPGQKGQANATRIPAKTPPAPKTPPSSGEPPKSGDRSGYSSPGSPG
TPGSRSRTPSLPTPPTREPKKVAVVRTPPKSPSSAKSRLQTAPVPMPDLKN
VKSKIGSTENLKHQPGGGKVQIINKKLDLSNVQSKCGSKDNIKHVPGGGSV
QIVYKPVDLSKVTSKCGSLGNIHHKPGGGQVEVKSEKLDFKDRVQSKIGSL
DNITHVPGGGNKKIETHKLTFRENAKAKTDHGAEIVYKSPVVSGDTSPRHL
SNVSSTGSIDMVDSPQLATLADEVSASLAKQGL SEQ ID No 11. Tau MBD1 aa: 243-274:
LQTAPVPMPDLKNVKSKIGSTENLKHQPGGGK SEQ ID No 12. Tau MBD2 aa: 275-305:
VQIINKKLDLSNVQSKCGSKDNIKHVPGGGS SEQ ID No 13. Tau MBD3 aa: 306-336:
VQIVYKPVDLSKVTSKCGSLGNIHHKPGGGQ SEQ ID No 14. Tau MBD4 aa: 337-368:
VEVKSEKLDFKDRVQSKIGSLDNITHVPGGGN

---

The invention claimed is:

1. A method for purifying nucleic acid molecules in a sample, comprising at least the step of:
   a) contacting said sample with at least one tubulin and one or more nucleic acid-trapping proteins comprising a nucleic acid-binding moiety and a polymerized tubulin-binding moiety under conditions for forming polymerized tubulin in complex with the one or more nucleic acid-trapping proteins bound to the said nucleic acids to be purified; and
   b) recovering nucleic acid-trapping protein(s) which is/are bound to the nucleic acid molecules, thereby purifying said nucleic acid molecules.

2. The method according to claim 1, wherein the nucleic acid molecule(s) is/are RNA molecule(s) and the one or more nucleic acid-trapping proteins is/are RNA-trapping proteins.

3. The method for purifying nucleic acid molecules according to claim 1, wherein in step a):
   the one or more nucleic acid-trapping proteins is/are added in vitro to the sample prior to immobilization on polymerized tubulin; or
   the sample comprises cells expressing said one or more nucleic acid-trapping proteins.

4. The method according to claim 1, wherein the one or more nucleic acid-trapping proteins is/are immobilized on tubulin.

5. The method according to claim 1, wherein the polymerized tubulin-binding moiety comprised in a nucleic acid-trapping protein comprises one or more Microtubule Binding Domains (MBDs) present in at least one protein selected from the group consisting of: Tau, MAP1A, MAP2, MAP4, MAP6 and EB1.

6. The method according to claim 1, wherein the nucleic acid-binding moiety comprises one or more nucleic acid-binding domains present in at least one protein selected from the group consisting of: TDP43, FUS, TAF15, NF45/NF90, DDX6, hnNRP A1, DHX36, FMRP, HuD, hnRNP L, HUR, G3BP1, Lin28A, Lin28B, AGO, HuR, METTL3, METTL14, FTO, ALKBH, YTHDF1-3, PABP1 and YBX1.

7. The method according to claim 1, wherein the one or more nucleic acid-trapping proteins comprises a linker region located between the nucleic acid-binding moiety and the polymerized tubulin-binding moiety.

8. The method according to claim 1, wherein step b) comprises expressing the one or more nucleic acid-trapping proteins in eukaryotic cells and recovering nucleic acid-trapping protein(s) which is/are bound to the nucleic acid molecules, thereby purifying said nucleic acid molecules.

9. The method according to claim 1, further comprising a step of collecting the nucleic acid molecules which are complexed with the one or more nucleic acid-trapping protein(s).

10. A method for characterizing nucleic acid molecules in a sample, comprising at least the steps of:
   a) contacting said sample with at least one tubulin and one or more nucleic acid-trapping proteins comprising a nucleic acid-binding moiety and a polymerized tubulin-binding moiety, under conditions for forming polymerized tubulin in complex with the one or more nucleic acid-trapping proteins bound to the nucleic acids molecules;
   b) recovering nucleic acid-trapping protein(s) which is/are bound to the nucleic acid molecules, thereby purifying said nucleic acid molecules; and
   c) characterizing the purified nucleic acid molecules.

11. The method according to claim 10, further comprising a step of collecting the nucleic acid molecules which are bound to the one or more nucleic acid-trapping protein(s).

12. A method for comparing the amounts of target nucleic acid molecules between two samples comprising at least the steps of:
   a) performing a method for purifying nucleic acid molecules according to claim 1 on a first sample by using a selected nucleic acid-trapping protein, so as to obtain a first collection of purified target nucleic acid molecules,
   b) performing a method for purifying nucleic acid molecules according to claim 1 on a second sample by using the same selected nucleic acid-trapping molecule as that used at step a), so as to obtain a second collection of purified target nucleic acid molecules, and
   c) determining the amount of target nucleic acid molecules comprised in the first collection of purified target nucleic acid molecules and in the second collection of purified target nucleic acid molecules, respectively.

* * * * *

SEQUENCE LISTING

<160> NUMBER OF SEQ ID NOS: 14

<210> SEQ ID NO 1
<211> LENGTH: 250
<212> TYPE: PRT
<213> ORGANISM: Homo sapiens

<400> SEQUENCE: 1

Ile Ala Thr Pro Arg Gly Ala Ala Pro Pro Gly Gln Lys Gly Gln Ala
1               5                   10                  15

Asn Ala Thr Arg Ile Pro Ala Lys Thr Pro Pro Ala Pro Lys Thr Pro
            20                  25                  30

Pro Ser Ser Gly Glu Pro Pro Lys Ser Gly Asp Arg Ser Gly Tyr Ser
        35                  40                  45

Ser Pro Gly Ser Pro Gly Thr Pro Gly Ser Arg Ser Arg Thr Pro Ser
    50                  55                  60

Leu Pro Thr Pro Pro Thr Arg Glu Pro Lys Lys Val Ala Val Val Arg
65                  70                  75                  80

Thr Pro Pro Lys Ser Pro Ser Ser Ala Lys Ser Arg Leu Gln Thr Ala
            85                  90                  95

Pro Val Pro Met Pro Asp Leu Lys Asn Val Lys Ser Lys Ile Gly Ser
            100                 105                 110

Thr Glu Asn Leu Lys His Gln Pro Gly Gly Gly Lys Val Gln Ile Ile
            115                 120                 125

Asn Lys Lys Leu Asp Leu Ser Asn Val Gln Ser Lys Cys Gly Ser Lys
130                 135                 140

Asp Asn Ile Lys His Val Pro Gly Gly Gly Ser Val Gln Ile Val Tyr
145                 150                 155                 160

Lys Pro Val Asp Leu Ser Lys Val Thr Ser Lys Cys Gly Ser Leu Gly
                165                 170                 175

Asn Ile His His Lys Pro Gly Gly Gly Gln Val Glu Val Lys Ser Glu
            180                 185                 190

Lys Leu Asp Phe Lys Asp Arg Val Gln Ser Lys Ile Gly Ser Leu Asp
            195                 200                 205

Asn Ile Thr His Val Pro Gly Gly Gly Asn Lys Lys Ile Glu Thr His
210                 215                 220

Lys Leu Thr Phe Arg Glu Asn Ala Lys Ala Lys Thr Asp His Gly Ala
225                 230                 235                 240

Glu Ile Val Tyr Lys Ser Pro Val Val Ser
                245                 250

<210> SEQ ID NO 2
<211> LENGTH: 358
<212> TYPE: PRT
<213> ORGANISM: Homo sapiens

<400> SEQUENCE: 2

Gln Asn Lys Ile Leu Glu Gly Leu Glu Lys Leu Arg His Leu Asp Phe
1               5                   10                  15

Leu Arg Tyr Pro Val Ala Thr Gln Lys Asp Leu Ala Ser Gly Ala Val
            20                  25                  30

Pro Thr Asn Leu Lys Pro Ser Lys Ile Lys Gln Arg Ala Asp Ser Lys
            35                  40                  45

Glu Ser Leu Lys Ala Thr Thr Lys Thr Ala Val Ser Lys Leu Ala Lys
50                  55                  60

Arg Glu Glu Val Val Glu Glu Gly Ala Lys Glu Ala Arg Ser Glu Leu
65                  70                  75                  80

Ala Lys Glu Leu Ala Lys Thr Glu Lys Lys Ala Lys Glu Ser Ser Glu
            85                  90                  95

Lys Pro Pro Glu Lys Pro Ala Lys Pro Glu Arg Val Lys Thr Glu Ser
            100                 105                 110

Ser Glu Ala Leu Lys Ala Glu Lys Arg Lys Leu Ile Lys Asp Lys Val
            115                 120                 125

Gly Lys Lys His Leu Lys Glu Lys Ile Ser Lys Leu Glu Glu Lys Lys
130                 135                 140

Asp Lys Glu Lys Lys Glu Ile Lys Lys Glu Arg Lys Glu Leu Lys Lys
145                 150                 155                 160

Asp Glu Gly Arg Lys Glu Glu Lys Lys Asp Ala Lys Lys Glu Glu Lys
            165                 170                 175

Arg Lys Asp Thr Lys Pro Glu Leu Lys Lys Ile Ser Lys Pro Asp Leu

```
                    180                 185                 190
Lys Pro Phe Thr Pro Glu Val Arg Lys Thr Leu Tyr Lys Ala Lys Val
            195                 200                 205

Pro Gly Arg Val Lys Ile Asp Arg Ser Arg Ala Ile Arg Gly Glu Lys
        210                 215                 220

Glu Leu Ser Ser Glu Pro Gln Thr Pro Ala Gln Lys Gly Thr Val
225                 230                 235                 240

Pro Leu Pro Thr Ile Ser Gly His Arg Glu Leu Val Leu Ser Ser Pro
                245                 250                 255

Glu Asp Leu Thr Gln Asp Phe Glu Glu Met Lys Arg Glu Glu Arg Ala
            260                 265                 270

Leu Leu Ala Glu Gln Arg Asp Thr Gly Leu Gly Asp Lys Pro Phe Pro
        275                 280                 285

Leu Asp Thr Ala Glu Gly Pro Pro Ser Thr Ala Ile Gln Gly Thr
            290                 295                 300

Pro Pro Ser Val Pro Gly Leu Gly Gln Glu Glu His Val Met Lys Glu
305                 310                 315                 320

Lys Glu Leu Val Pro Glu Val Pro Glu Glu Gln Gly Ser Lys Asp Arg
                325                 330                 335

Gly Leu Asp Ser Gly Ala Glu Thr Glu Glu Lys Asp Thr Trp Glu
            340                 345                 350

Glu Lys Lys Gln Arg Glu
        355

<210> SEQ ID NO 3
<211> LENGTH: 308
<212> TYPE: PRT
<213> ORGANISM: Homo sapiens

<400> SEQUENCE: 3

Phe Lys Gln Ala Lys Asp Lys Val Ser Asp Gly Val Thr Lys Ser Pro
1               5                   10                  15

Glu Lys Arg Ser Ser Leu Pro Arg Pro Ser Ser Ile Leu Pro Pro Arg
            20                  25                  30

Arg Gly Val Ser Gly Asp Arg Asp Glu Asn Ser Phe Ser Leu Asn Ser
        35                  40                  45

Ser Ile Ser Ser Ser Ala Arg Arg Thr Thr Arg Ser Glu Pro Ile Arg
    50                  55                  60

Arg Ala Gly Lys Ser Gly Thr Ser Thr Pro Thr Thr Pro Gly Ser Thr
65                  70                  75                  80

Ala Ile Thr Pro Gly Thr Pro Pro Ser Tyr Ser Ser Arg Thr Pro Gly
                85                  90                  95

Thr Pro Gly Thr Pro Ser Tyr Pro Arg Thr Pro His Thr Pro Gly Thr
            100                 105                 110

Pro Lys Ser Ala Ile Leu Val Pro Ser Glu Lys Lys Val Ala Ile Ile
        115                 120                 125

Arg Thr Pro Pro Lys Ser Pro Ala Thr Pro Lys Gln Leu Arg Leu Ile
    130                 135                 140

Asn Gln Pro Leu Pro Asp Leu Lys Asn Val Lys Ser Lys Ile Gly Ser
145                 150                 155                 160

Thr Asp Asn Ile Lys Tyr Gln Pro Lys Gly Gly Gln Val Gln Ile Val
                165                 170                 175

Thr Lys Lys Ile Asp Leu Ser His Val Thr Ser Lys Cys Gly Ser Leu
            180                 185                 190
```

```
Lys Asn Ile Arg His Arg Pro Gly Gly Arg Val Lys Ile Glu Ser
            195                 200                 205

Val Lys Leu Asp Phe Lys Glu Lys Ala Gln Ala Lys Val Gly Ser Leu
    210                 215                 220

Asp Asn Ala His His Val Pro Gly Gly Gly Asn Val Lys Ile Asp Ser
225                 230                 235                 240

Gln Lys Leu Asn Phe Arg Glu His Ala Lys Ala Arg Val Asp His Gly
            245                 250                 255

Ala Glu Ile Ile Thr Gln Ser Pro Gly Arg Ser Ser Val Ala Ser Pro
            260                 265                 270

Arg Arg Leu Ser Asn Val Ser Ser Gly Ser Ile Asn Leu Leu Glu
            275                 280                 285

Ser Pro Gln Leu Ala Thr Leu Ala Glu Asp Val Thr Ala Ala Leu Ala
    290                 295                 300

Lys Gln Gly Leu
305

<210> SEQ ID NO 4
<211> LENGTH: 162
<212> TYPE: PRT
<213> ORGANISM: Homo sapiens

<400> SEQUENCE: 4

Leu Ala Thr Asn Thr Ser Ala Pro Asp Leu Lys Asn Val Arg Ser Lys
1               5                   10                  15

Val Gly Ser Thr Glu Asn Ile Lys His Gln Pro Gly Gly Gly Arg Ala
            20                  25                  30

Lys Val Glu Lys Lys Thr Glu Ala Ala Ala Thr Thr Arg Lys Pro Glu
        35                  40                  45

Ser Asn Ala Val Thr Lys Thr Ala Gly Pro Ile Ala Ser Ala Gln Lys
    50                  55                  60

Gln Pro Ala Gly Lys Val Gln Ile Val Ser Lys Lys Val Ser Tyr Ser
65                  70                  75                  80

His Ile Gln Ser Lys Cys Gly Ser Lys Asp Asn Ile Lys His Val Pro
                85                  90                  95

Gly Gly Gly Asn Val Gln Ile Gln Asn Lys Lys Val Asp Ile Ser Lys
            100                 105                 110

Val Ser Ser Lys Cys Gly Ser Lys Ala Asn Ile Lys His Lys Pro Gly
        115                 120                 125

Gly Gly Asp Val Lys Ile Glu Ser Gln Lys Leu Asn Phe Lys Glu Lys
    130                 135                 140

Ala Gln Ala Lys Val Gly Ser Leu Asp Asn Val Gly His Leu Pro Ala
145                 150                 155                 160

Gly Gly

<210> SEQ ID NO 5
<211> LENGTH: 203
<212> TYPE: PRT
<213> ORGANISM: Homo sapiens

<400> SEQUENCE: 5

Ser Val Met Arg Gln Asp Tyr Arg Ala Trp Lys Val Gln Arg Pro Glu
1               5                   10                  15

Pro Ser Cys Arg Pro Arg Ser Glu Tyr Gln Pro Ser Asp Ala Pro Phe
            20                  25                  30

Glu Arg Glu Thr Gln Tyr Gln Lys Asp Phe Arg Ala Trp Pro Leu Pro
```

```
                35                  40                  45
Arg Arg Gly Asp His Pro Trp Ile Pro Lys Pro Val Gln Ile Ser Ala
 50                  55                  60

Ala Ser Gln Ala Ser Ala Pro Ile Leu Gly Ala Pro Lys Arg Arg Pro
 65                  70                  75                  80

Gln Ser Gln Glu Arg Trp Pro Val Gln Ala Ala Glu Ala Arg Glu
                 85                  90                  95

Gln Glu Ala Ala Pro Gly Gly Ala Gly Gly Leu Ala Ala Gly Lys Ala
                100                 105                 110

Ser Gly Ala Asp Glu Arg Asp Thr Arg Arg Lys Ala Gly Pro Ala Trp
                115                 120                 125

Ile Val Arg Arg Ala Glu Gly Leu Gly His Glu Gln Thr Pro Leu Pro
            130                 135                 140

Ala Ala Gln Ala Gln Val Gln Ala Thr Gly Pro Glu Ala Gly Arg Gly
145                 150                 155                 160

Arg Ala Ala Ala Asp Ala Leu Asn Arg Gln Ile Arg Glu Glu Val Ala
                165                 170                 175

Ser Ala Val Ser Ser Tyr Arg Asn Glu Phe Arg Ala Trp Thr Asp
            180                 185                 190

Ile Lys Pro Val Lys Pro Ile Lys Ala Lys Pro
            195                 200
```

```
<210> SEQ ID NO 6
<211> LENGTH: 145
<212> TYPE: PRT
<213> ORGANISM: Homo sapiens

<400> SEQUENCE: 6

Tyr Asp Pro Val Ala Ala Arg Gln Gly Gln Glu Thr Ala Val Ala Pro
 1               5                  10                  15

Ser Leu Val Ala Pro Ala Leu Asn Lys Pro Lys Lys Pro Leu Thr Ser
                 20                  25                  30

Ser Ser Ala Ala Pro Gln Arg Pro Ile Ser Thr Gln Arg Thr Ala Ala
             35                  40                  45

Ala Pro Lys Ala Gly Pro Gly Val Val Arg Lys Asn Pro Gly Val Gly
         50                  55                  60

Asn Gly Asp Asp Glu Ala Ala Glu Leu Met Gln Gln Val Asn Val Leu
 65                  70                  75                  80

Lys Leu Thr Val Glu Asp Leu Glu Lys Glu Arg Asp Phe Tyr Phe Gly
                 85                  90                  95

Lys Leu Arg Asn Ile Glu Leu Ile Cys Gln Glu Asn Glu Gly Glu Asn
                100                 105                 110

Asp Pro Val Leu Gln Arg Ile Val Asp Ile Leu Tyr Ala Thr Asp Glu
            115                 120                 125

Gly Phe Val Ile Pro Asp Glu Gly Gly Pro Gln Glu Glu Gln Glu Glu
            130                 135                 140

Tyr
145
```

```
<210> SEQ ID NO 7
<211> LENGTH: 451
<212> TYPE: PRT
<213> ORGANISM: Homo sapiens

<400> SEQUENCE: 7

Met Arg Glu Cys Ile Ser Ile His Val Gly Gln Ala Gly Val Gln Ile
```

```
1               5                   10                  15
Gly Asn Ala Cys Trp Glu Leu Tyr Cys Leu Glu His Gly Ile Gln Pro
            20                  25                  30
Asp Gly Gln Met Pro Ser Asp Lys Thr Ile Gly Gly Gly Asp Asp Ser
            35                  40                  45
Phe Asn Thr Phe Phe Ser Glu Thr Gly Ala Gly Lys His Val Pro Arg
            50                  55                  60
Ala Val Phe Val Asp Leu Glu Pro Thr Val Ile Asp Glu Val Arg Thr
65                  70                  75                  80
Gly Thr Tyr Arg Gln Leu Phe His Pro Glu Gln Leu Ile Thr Gly Lys
                85                  90                  95
Glu Asp Ala Ala Asn Asn Tyr Ala Arg Gly His Tyr Thr Ile Gly Lys
            100                 105                 110
Glu Ile Ile Asp Leu Val Leu Asp Arg Ile Arg Lys Leu Ala Asp Gln
            115                 120                 125
Cys Thr Arg Leu Gln Gly Phe Leu Val Phe His Ser Phe Gly Gly Gly
            130                 135                 140
Thr Gly Ser Gly Phe Thr Ser Leu Leu Met Glu Arg Leu Ser Val Asp
145                 150                 155                 160
Tyr Gly Lys Lys Ser Lys Leu Glu Phe Ser Ile Tyr Pro Ala Pro Gln
                165                 170                 175
Val Ser Thr Ala Val Val Glu Pro Tyr Asn Ser Ile Leu Thr Thr His
            180                 185                 190
Thr Thr Leu Glu His Ser Asp Cys Ala Phe Met Val Asp Asn Glu Ala
            195                 200                 205
Ile Tyr Asp Ile Cys Arg Arg Asn Leu Asp Ile Glu Arg Pro Thr Tyr
            210                 215                 220
Thr Asn Leu Asn Arg Leu Ile Ser Gln Ile Val Ser Ser Ile Thr Ala
225                 230                 235                 240
Ser Leu Arg Phe Asp Gly Ala Leu Asn Val Asp Leu Thr Glu Phe Gln
                245                 250                 255
Thr Asn Leu Val Pro Tyr Pro Arg Ile His Phe Pro Leu Ala Thr Tyr
            260                 265                 270
Ala Pro Val Ile Ser Ala Glu Lys Ala Tyr His Glu Gln Leu Ser Val
            275                 280                 285
Ala Asp Ile Thr Asn Ala Cys Phe Glu Pro Ala Asn Gln Met Val Lys
            290                 295                 300
Cys Asp Pro Gly His Gly Lys Tyr Met Ala Cys Cys Leu Leu Tyr Arg
305                 310                 315                 320
Gly Asp Val Val Pro Lys Asp Val Asn Ala Ala Ile Ala Thr Ile Lys
                325                 330                 335
Thr Lys Arg Thr Ile Gln Phe Val Asp Trp Cys Pro Thr Gly Phe Lys
            340                 345                 350
Val Gly Ile Asn Tyr Gln Pro Pro Thr Val Val Pro Gly Gly Asp Leu
            355                 360                 365
Ala Lys Val Gln Arg Ala Val Cys Met Leu Ser Asn Thr Thr Ala Ile
            370                 375                 380
Ala Glu Ala Trp Ala Arg Leu Asp His Lys Phe Asp Leu Met Tyr Ala
385                 390                 395                 400
Lys Arg Ala Phe Val His Trp Tyr Val Gly Glu Gly Met Glu Glu Gly
                405                 410                 415
Glu Phe Ser Glu Ala Arg Glu Asp Met Ala Ala Leu Glu Lys Asp Tyr
            420                 425                 430
```

Glu Val Gly Val Asp Ser Val Glu Gly Glu Gly Glu Glu Gly
    435                 440                 445

Glu Glu Tyr
    450

<210> SEQ ID NO 8
<211> LENGTH: 444
<212> TYPE: PRT
<213> ORGANISM: Homo sapiens

<400> SEQUENCE: 8

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
        35                  40                  45

Val Tyr Tyr Asn Glu Ala Thr Gly Gly Lys Tyr Val Pro Arg Ala Ile
50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Arg Leu Thr Thr Pro Thr Tyr Gly Asp
    210                 215                 220

Leu Asn His Leu Val Ser Gly Thr Met Glu Cys Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Asp
        275                 280                 285

Leu Thr Gln Gln Val Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala

```
            340                 345                 350
Val Cys Asp Ile Pro Pro Arg Gly Leu Lys Met Ala Val Thr Phe Ile
            355                 360                 365

Gly Asn Ser Thr Ala Ile Gln Glu Leu Phe Lys Arg Ile Ser Glu Gln
        370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Glu Asp Phe Gly Glu Glu Ala Glu Glu Ala
        435                 440
```

<210> SEQ ID NO 9
<211> LENGTH: 150
<212> TYPE: PRT
<213> ORGANISM: Homo sapiens

<400> SEQUENCE: 9

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys
145                 150
```

<210> SEQ ID NO 10
<211> LENGTH: 441
<212> TYPE: PRT
<213> ORGANISM: Homo sapiens

<400> SEQUENCE: 10

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
```

```
            65                  70                  75                  80
Asp Glu Gly Ala Pro Gly Lys Gln Ala Ala Gln Pro His Thr Glu
                85                  90                  95
Ile Pro Glu Gly Thr Ala Glu Ala Gly Ile Gly Asp Thr Pro
            100                 105                 110
Ser Leu Glu Asp Glu Ala Ala Gly His Val Thr Gln Ala Arg Met Val
                115                 120                 125
Ser Lys Ser Lys Asp Gly Thr Gly Ser Asp Lys Lys Ala Lys Gly
            130                 135                 140
Ala Asp Gly Lys Thr Lys Ile Ala Thr Pro Arg Gly Ala Ala Pro
145                 150                 155                 160
Gly Gln Lys Gly Gln Ala Asn Ala Thr Arg Ile Pro Ala Lys Thr Pro
                165                 170                 175
Pro Ala Pro Lys Thr Pro Ser Ser Gly Glu Pro Lys Ser Gly
            180                 185                 190
Asp Arg Ser Gly Tyr Ser Ser Pro Gly Ser Pro Gly Thr Pro Gly Ser
                195                 200                 205
Arg Ser Arg Thr Pro Ser Leu Pro Thr Pro Pro Thr Arg Glu Pro Lys
210                 215                 220
Lys Val Ala Val Val Arg Thr Pro Pro Lys Ser Pro Ser Ser Ala Lys
225                 230                 235                 240
Ser Arg Leu Gln Thr Ala Pro Val Pro Met Pro Asp Leu Lys Asn Val
                245                 250                 255
Lys Ser Lys Ile Gly Ser Thr Glu Asn Leu Lys His Gln Pro Gly Gly
                260                 265                 270
Gly Lys Val Gln Ile Ile Asn Lys Lys Leu Asp Leu Ser Asn Val Gln
            275                 280                 285
Ser Lys Cys Gly Ser Lys Asp Asn Ile Lys His Val Pro Gly Gly Gly
            290                 295                 300
Ser Val Gln Ile Val Tyr Lys Pro Val Asp Leu Ser Lys Val Thr Ser
305                 310                 315                 320
Lys Cys Gly Ser Leu Gly Asn Ile His His Lys Pro Gly Gly Gly Gln
                325                 330                 335
Val Glu Val Lys Ser Glu Lys Leu Asp Phe Lys Asp Arg Val Gln Ser
                340                 345                 350
Lys Ile Gly Ser Leu Asp Asn Ile Thr His Val Pro Gly Gly Gly Asn
            355                 360                 365
Lys Lys Ile Glu Thr His Lys Leu Thr Phe Arg Glu Asn Ala Lys Ala
370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
                420                 425                 430
Ser Ala Ser Leu Ala Lys Gln Gly Leu
            435                 440

<210> SEQ ID NO 11
<211> LENGTH: 32
<212> TYPE: PRT
<213> ORGANISM: Homo sapiens

<400> SEQUENCE: 11
```

```
Leu Gln Thr Ala Pro Val Pro Met Pro Asp Leu Lys Asn Val Lys Ser
1               5                   10                  15

Lys Ile Gly Ser Thr Glu Asn Leu Lys His Gln Pro Gly Gly Lys
            20                  25                  30

<210> SEQ ID NO 12
<211> LENGTH: 31
<212> TYPE: PRT
<213> ORGANISM: Homo sapiens

<400> SEQUENCE: 12

Val Gln Ile Ile Asn Lys Lys Leu Asp Leu Ser Asn Val Gln Ser Lys
1               5                   10                  15

Cys Gly Ser Lys Asp Asn Ile Lys His Val Pro Gly Gly Ser
            20                  25                  30

<210> SEQ ID NO 13
<211> LENGTH: 31
<212> TYPE: PRT
<213> ORGANISM: Homo sapiens

<400> SEQUENCE: 13

Val Gln Ile Val Tyr Lys Pro Val Asp Leu Ser Lys Val Thr Ser Lys
1               5                   10                  15

Cys Gly Ser Leu Gly Asn Ile His His Lys Pro Gly Gly Gly Gln
            20                  25                  30

<210> SEQ ID NO 14
<211> LENGTH: 32
<212> TYPE: PRT
<213> ORGANISM: Homo sapiens

<400> SEQUENCE: 14

Val Glu Val Lys Ser Glu Lys Leu Asp Phe Lys Asp Arg Val Gln Ser
1               5                   10                  15

Lys Ile Gly Ser Leu Asp Asn Ile Thr His Val Pro Gly Gly Gly Asn
            20                  25                  30
```